United States Patent
Kwan et al.

(10) Patent No.: US 8,937,554 B2
(45) Date of Patent: Jan. 20, 2015

(54) LOW POWER LOCATION-TRACKING DEVICE WITH COMBINED SHORT-RANGE AND WIDE-AREA WIRELESS AND LOCATION CAPABILITIES

(75) Inventors: Dennis Kwan, San Diego, CA (US); Suresh Singamsetty, Aliso Viejo, CA (US); Jeffrey Hsieh, Dove Canyon, CA (US)

(73) Assignee: SilverPlus, Inc., Irvine, CA (US)

( * ) Notice: Subject to any disclaimer, the term of this patent is extended or adjusted under 35 U.S.C. 154(b) by 424 days.

(21) Appl. No.: 13/200,687

(22) Filed: Sep. 28, 2011

(65) Prior Publication Data

US 2013/0076523 A1 Mar. 28, 2013

(51) Int. Cl.
*G08B 21/00* (2006.01)
*G08B 25/01* (2006.01)
*A61B 5/00* (2006.01)
(Continued)

(52) U.S. Cl.
CPC ............ *G08B 25/016* (2013.01); *A61B 5/0022* (2013.01); *A61B 5/1112* (2013.01); *A61B 5/1117* (2013.01); *A61B 5/1118* (2013.01); *G08B 21/0247* (2013.01);
(Continued)

(58) Field of Classification Search
CPC ........... G08B 21/0288; G08B 13/2462; G08B 21/0286; G08B 21/25016; A61B 5/0022; G06K 2017/0045; H04W 4/00; G01C 21/16
USPC ............. 340/539.15, 539.13, 539.23, 539.32, 340/572.1, 573.4, 636.1; 375/219
See application file for complete search history.

(56) References Cited

U.S. PATENT DOCUMENTS 4,858,622 A 8/1989 Osterweil
5,204,670 A * 4/1993 Stinton ........................ 340/10.5
(Continued)

FOREIGN PATENT DOCUMENTS

WO WO 99/19742 4/1999
WO WO 2008/152588 12/2008

OTHER PUBLICATIONS

PCT Search Report PCT/US2012/057189 Mail date—Feb. 26, 2013, Silverplus, Inc.
(Continued)

*Primary Examiner* — Phung Nguyen
(74) *Attorney, Agent, or Firm* — Saile Ackerman LLC; Stephen B. Ackerman; Billy Knowles

(57) ABSTRACT

A personal monitoring and communication system includes a monitoring and communication control device, at least one personal monitoring communication device coupled with a person and a personal monitoring communication device finder. The personal monitoring communication device includes a GPS receiver, cellular telephone circuits, and short-range wireless radio circuits for communicating with caregivers. The personal monitoring communication device finder receives an emergency beacon generated by one personal monitoring communication device and determines a location of the personal monitoring communication device. A dead reckoning circuit determines the position of the person from a reference location. A motion detection circuit determines that the person is moving, not moving, or has fallen. A battery power management circuit minimizes power consumption to increase battery life of a battery powering the personal monitoring communication device. A tamper detection circuit determines whether the personal monitoring communication device is coupled to the person.

85 Claims, 13 Drawing Sheets

(51) Int. Cl.
*A61B 5/11* (2006.01)
*G08B 21/02* (2006.01)
*G08B 21/04* (2006.01)

(52) U.S. Cl.
CPC ........ *G08B 21/0286* (2013.01); *G08B 21/0446* (2013.01); *A61B 2560/0209* (2013.01)
USPC .................................................... 340/686.6

(56) References Cited

U.S. PATENT DOCUMENTS

| | | | |
|---|---|---|---|
| 5,458,123 | A | 10/1995 | Unger |
| 6,072,784 | A | 6/2000 | Agrawal et al. |
| 6,239,700 | B1* | 5/2001 | Hoffman et al. ......... 340/539.13 |
| 6,414,626 | B1 | 7/2002 | Greef et al. |
| 6,459,402 | B1 | 10/2002 | Tsunehara et al. |
| 6,657,579 | B2 | 12/2003 | Tsunehara et al. |
| 6,731,908 | B2 | 5/2004 | Berliner et al. |
| 6,801,159 | B2 | 10/2004 | Swope et al. |
| 7,365,645 | B2 | 4/2008 | Heinze et al. |
| 7,561,048 | B2 | 7/2009 | Yushkov et al. |
| 7,663,532 | B2 | 2/2010 | Tsunehara et al. |
| 7,761,233 | B2* | 7/2010 | Schott et al. ................... 701/434 |
| 7,872,583 | B1 | 1/2011 | Yushkov et al. |
| 7,945,297 | B2 | 5/2011 | Philipp |
| 2001/0026240 | A1 | 10/2001 | Neher |
| 2002/0036569 | A1* | 3/2002 | Martin ........................ 340/573.1 |
| 2005/0033200 | A1 | 2/2005 | Soehren et al. |
| 2007/0222588 | A1* | 9/2007 | Wolfe ...................... 340/539.13 |
| 2008/0045806 | A1 | 2/2008 | Keppler |
| 2008/0077326 | A1* | 3/2008 | Funk et al. .................... 701/220 |
| 2008/0252527 | A1 | 10/2008 | Garcia |
| 2009/0224909 | A1* | 9/2009 | Derrick et al. ........... 340/539.13 |
| 2010/0202327 | A1 | 8/2010 | Mushkin et al. |
| 2010/0207820 | A1 | 8/2010 | Kawano et al. |
| 2010/0295674 | A1 | 11/2010 | Hsieh et al. |
| 2010/0295684 | A1 | 11/2010 | Hsieh et al. |

OTHER PUBLICATIONS

"Spread Spectrum (SS)," Hogeschool Voor Wetenschap & Kunst [De Nayer Instituut], by J. Meel, Sirius Communications—Rotselaar—Belgium, Studiedag Spread Spectrum—Oct. 6, 1999, pp. 1-33.

Co-pending U.S. Patent SP10-001, U.S. Appl. No. 13/066,787, filed Apr. 25, 2011, "Wireless System Networks with Local and Wide-Area Coverage," assigned to the same assignee as the present invention, 51 pgs.

"SGW66i GPS Watch Personal Locator," LifePROTEKT, found Apr. 18, 2011, http://wwwlifeprotekt.com/sgw66i-gps-watch-phone-touchscreen-child-locator/11pgs.

"BrickHouse Alert Mobile GPS," BrickHouse Alert, found Apr. 18, 2011, http://www.brickhousealert.com/medical-alarm-gps-tracking-bracelets.html, 2 pgs.

"S-911 Bracelet Locator HC," Health Care, LAIPAC Tech, ASIS10 accolades, found Apr. 18, 2011, http://www.laipac.com/bracelet_locator_gps.htm, 4 pgs.

Smart Antennas for Wireless Communications,Chapter 7. pp. 169-201, by F.B. Gross, McGraw Hill, Inc., New York, NY, 2005.

"Basic Inertial Navigation," by Sherryl H. Stovall, NAWCWPNS TM 8128, Sep. 1997, Naval Air Warface Center Weapons Center Weapons Division, China Lake, CA, pp. 1-34.

"GPS Locators bring peace of mind for many," GPS-practice-and-fun.com, found Apr. 18, 2011, http://www.gps-practice-and-fun.com/gps-locators.html, pp. 1-15.

"The Escort System: A Safety monitor for People Living with Alzheimer's," by D. Taub et al., IEEE Xplore Digital Library, found Apr. 13, 2011, p. 68-76, found Apr. 13, 2011, http://ieeexplore.ieee.org/search/srchabstract.jsp?p=&arnumber=554 . . . .

"Patient tracking system," by H. Gamboa et al., IEEE Xplore Digital Library, found Apr. 13, 2011, 2 pgs.

"iWander: An Android Application for dementia patients," by F. Sposaro et al., IEEE Xplore Digital Library, found Apr. 13, 2011, p. 3875-3878, http://ieeexplore.ieee.org/search/srchabstract.jsp?p=&arnumbers=562 . . . .

"Energy-aware wireless microsensor networks," by V. Raghunathan et al., IEEE Xplore Digital Library, found Apr. 13, 2011, p. 1-10 index & , 40-50, http://ieeexplore.ieee.org/xpls/abs_all.jsp?arnymber=985679.

"Methods of improving accuracy of indoor-localization systems based on 802.11 standard infrastucture," by P. Przytula et al., IEEE Xplore Digital Library, found Apr. 13, 2011, 5 pgs., http://ieeexplore.ieee.org/xpls/abs_all.jsp?arnumber=4630204.

"A survey of indoor positioning systmes for wireless personal networks," by Gu Yanying et al., IEEE Xplore Digital Library, found Apr. 13, 2011, p. 13-32, http://ieeexplore.ieee.org/search/srchabstract.jsp? tp=&arnumber=543 . . . .

"Enhancements to RSS Based Indoor Tracking Systems Using Kalman Filters," by I. Guvenc et al., 6pgs., International Expo (GPx), Mar. 31-Apr. 3, 2003, Dallas, TX, Copyright 2003 GSPx.

Global Positioning Systems, Inertial Navigation, and Integration, Second Edition, by Mohinder S. Grewal et al., Wiley-Interscience, A John Wiley & Sons, Inc. Publication, Copyright 2007, Chapter 6, pp. 131-178.

* cited by examiner

| | SRLAWN | Cellular | GPS |
|---|---|---|---|
| IDLE INDOOR (915) | Sync to beacon from MCCD | Off | Off |
| SYNC SEARCH INDOOR (905) | Search for beacon from MCCD | On | On |
| ACTIVE OUTDOOR (925) | Off | On | On |
| ACTIVE WAITING OUTDOOR (935) | Off | Standby | Standby |
| LOW-POWER OUTDOOR (975) | Off | Standby | Standby |
| IDLE OUTDOOR (990) | Off | Standby | Off |
| ACTIVE BEACON (950) | Beacon Tx | Search for Cellular | Off |
| LOW-POWER BEACON (960) | Intermittend beacon Tx | Off | Off |

FIG. 14

LOW POWER LOCATION-TRACKING DEVICE WITH COMBINED SHORT-RANGE AND WIDE-AREA WIRELESS AND LOCATION CAPABILITIES

RELATED PATENT APPLICATIONS

U.S. patent application Ser. No. 12/454,714 (714), filed on May 21, 2009, assigned to the same assignee as the present invention, and incorporated herein by reference in its entirety.

U.S. patent application Ser. No. 12/454,715 (715), filed on May 21, 2009, assigned to the same assignee as the present invention, and incorporated herein by reference in its entirety.

U.S. patent application Ser. No. 13/066,787 (787), filed on Apr. 25, 2011, assigned to the same assignee as the present invention, and incorporated herein by reference in its entirety.

BACKGROUND OF THE INVENTION

1. Field of the Invention

This invention relates generally to electronic monitoring and communication systems. More particularly, this invention relates to an electronic monitoring and communication system providing wireless radio frequency communication circuits and methods, emergency radio frequency location circuits and methods, personal dead reckoning circuits and methods, battery power management circuits and methods, and tamper detection circuits and methods.

2. Description of Related Art

Electronic monitoring systems for remote monitoring and supervising of moving objects, and in particular for monitoring persons, are known in the art. The advantages of employing such a system in a wide range of applications in a variety of fields, including security, law enforcement, medical and more are known.

"SGW66i GPS Watch Personal Locator" sold by Lifeprotekt, found Apr. 18, 2011, www.lifeprotekt.com, "BrickHouse Alert Mobile GPS" sold by BrickHouse Alert, found Apr. 18, 2011, www.BrickHouseAlert.com, and "S-911 Bracelet Locator" manufactured by Laipac Technology Inc, Toronto, Ontario, Canada, L4B 1G5, are examples of personal location devices. These location tracking devices are used for tracking persons remotely by determining their location using satellite navigation systems such as GPS or GLONASS (hereafter referred to as GPS), and sending the location information over a cellular wireless system such as GSM or CDMA and digital wireless systems such as Bluetooth and Zigbee. These can be dedicated devices or just GPS-equipped cellular phones. Dedicated devices are often used as safety devices for tracking elderly people, who are indoors for a large proportion of their time. In most products, both the cellular and GPS are always powered, as long as the device is activated, and only rely on the power-saving modes of the individual cellular and GPS radios for lowering the power consumption as much as possible. This is not very efficient especially when the device is indoors and very often not being able to receive GPS signals, which causes the device to use even more power as the GPS receiver searches for signals. As a result most devices with a small form factor often have very poor battery life, ranging from a few hours to 2 or 3 days at most.

For personal location devices for persons requiring monitoring and are indoors or other areas where the GPS is not effective (i.e. outdoor "city canyons with large buildings), the GPS can only provide a location until the GPS signal is lost. For personal location devices having only cellular service for contacting monitoring personnel, often in large building, the cellular service is not functional. If the GPS and the cellular service are not functioning, the personal monitoring device is no longer functional.

If a monitored person has wandered, and has a problem and activates a "panic button" of the monitor system with no GPS function, there is no way of locating the person since the last GPS location is the last received GPS signal. The person may have wandered a significant distance. If the cellular system is working, where the person has wandered, a triangulation may be performed based on local cell towers. However, this triangulation is only accurate to 600 m or more. If the cellular service is not available where the person has wandered, there is no way of finding the person.

The reliability of the monitoring and communication system depends on the ability of the system to identify that the person being monitored has not tampered with the monitoring device. Persons such as criminal offenders, patients (i.e. mental illness patients, Alzheimer's patients, or infectious diseases patients), and children may cause difficulties since the monitored person may try to remove the monitoring device. The monitoring devices may be equipped with tamper detection sensors in order to prevent tampering with the tag. Tamper detection sensors now available may be divided into two groups: a strap cut sensor and a body or proximity sensor. Presently no other types of tampers related sensors are employed or are used in tags.

SUMMARY OF THE INVENTION

An object to this invention is to provide a personal monitoring and communication system and method for determining a person's location within an area where GPS is not able to be received.

Further, an object of this invention is to provide personal monitoring and communication system and method that will locate a person being monitored in an emergency.

Still further, an object of this invention is to provide personal monitoring and communication system and method with a short range wireless communication transmitter/receiver for communicating with a person being monitored.

Still further, an object of this invention is to provide personal monitoring and communication system and method with circuits and methods for detecting motion, lack of motion, and falling.

Still further, an object of this invention is to provide personal monitoring and communication system and method with circuits and methods for management of battery power of a device Even still further, an object of this invention is to provide personal monitoring and communication system and method including circuits and method for determining that the person being monitored has tampered with a device attached to the person's body.

To accomplish at least one of these objects, a personal monitoring and communication system includes at least one monitoring and communication control device in communication with at least one personal monitoring communication device that is coupled to a person or persons being monitored. The personal monitoring control device includes a global positioning system receiver, a cellular telephone radio transmitter/receiver, and a short range wireless radio transmitter/receiver. In some embodiments, the short range wireless radio transmitter/receiver provides the ability for is communicating with caregivers or supervisory personnel responsible for monitoring the person coupled to the personal monitoring communication device.

In various embodiments, the personal monitoring and communication system has a personal monitoring communication device finder. The personal monitoring communication device has an emergency beacon generator that is connected to a panic button, which when pressed by a person being monitored activates the emergency beacon generator that provides a frequency hopping signal at a slow hopping rate and includes an arbitrarily long pseudorandom bit sequence to the short range wireless radio transmitter/receiver. The long pseudorandom bit sequence has a bit repetition factor such that the bit repetition factor maximizes demodulation and detection probability by a receiver. The long pseudorandom bit sequence has a maximum value that is determined by a minimum signal bandwidth dictated by regulatory requirements. A product of a bit period multiplied by the bit repetition factor and the length of the long pseudorandom bit sequence determines a dwell time that is regulated. In some embodiments, the dwell time is 0.4 seconds.

In some embodiments, the personal monitoring communication device finder includes a slow frequency hopping sequence generator that provides a frequency sequence for a receiver that matches the slow hopping rate to receive the frequency hopping signal. The personal monitoring communication device finder has a frequency shift keying demodulator to extract the long pseudorandom bit sequence. The extracted long pseudorandom bit sequence and a local version of the long pseudorandom bit sequence are applied to a correlator. The correlator determines a sampling absolute correlation value for the extracted long pseudorandom bit sequence and the local long pseudorandom bit sequence. The sampling absolute correlation value gives an estimate of the distance of the personal monitoring communication device finder to the personal monitoring communication device transmitting the emergency beacon. The distance is determined as a function of the personal monitoring communication device transmit power, a gain of the receiver of the personal monitoring communication device finder, and a propagation path loss model. The personal monitoring communication is device finder has at least one directional antenna for determining a direction from the personal monitoring communication device finder to the personal monitoring communication device transmitting the emergency beacon. In some embodiments, the personal monitoring communication device finder has a display for presenting the distance and direction from the personal monitoring communication device finder to the personal monitoring communication device transmitting the emergency beacon. In other embodiments, the personal monitoring communication device finder has a sound producing device for presenting an audible indication of the distance and direction from the personal monitoring communication device finder to the personal monitoring communication device transmitting the emergency beacon.

In various embodiments, the monitoring and communication control device includes the personal monitoring communication device finder for determining the location of a personal monitoring communication device transmitting an emergency beacon.

In some embodiments, the personal monitoring communication device has a dead reckoning circuit for determining the position of the person coupled to the personal monitoring communication device when the global positioning system receiver is unable to determine the position. The short range wireless radio transmitter/receiver receives a signal from the monitoring and communication control device and from the signal the dead reckoning device establishes a reference location from at least one monitoring and communication control device. The dead reckoning circuit determines if a receiver signal strength indicator (RSSI) level for transmissions received by the personal monitoring and communication device from the monitoring and communication control device exceeds a threshold level. When the RSSI level exceeds a threshold hold level, the location is denoted as a reference location. The dead reckoning circuit has a gyroscope for determining a direction and a three-axis accelerometer for determining an acceleration vector when the person moves. The dead reckoning circuit has an integration unit that integrates the acceleration vector to determine a displacement. The direction and displacement are used to provide a dead reckoning location from the reference location.

All motions are measured accurately by the gyroscope and the three-axis accelerometer. The small scale wrist movements or large scale full body walking result in displacement vectors that form the path that the device has traveled. The gyroscope and three-axis accelerometer have the resolution, dynamic range, sampling frequency and accuracy for collecting accurate data detailing the movement of the dead reckoning circuit. Given accurate data, simple averaging and low-pass filtering of the displacement data removes small scale changes (high frequency) and extracts only the large scale changes (low frequency) for location determination.

In various embodiments, the personal monitoring communication device has a motion detection circuit for determining that the person to whom the personal monitoring communication device is coupled is moving, has not been in motion for an extended period of time, or has fallen. The motion detection circuit has a gyroscope and a three-axis accelerometer. The gyroscope provides a direction signal indicating a direction that the person is moving and the three-axis accelerometer provides signals indicating an acceleration vector. The motion detection circuit has a motion computation circuit that receives the direction signal and the acceleration vector signals and determines if the person is in motion, or if the person has been inactive for an extended period of time, or if the person has fallen.

In various embodiments, the personal monitoring communication device has a battery power management circuit for minimizing power consumption to increase battery life of a battery powering each of the personal monitoring communication devices of the personal monitoring and communication system. The battery power management circuit has a battery power sensing device for determining an amount of power remaining in the battery. The battery power management circuit monitors the status of the global positioning system receiver; the cellular telephone radio transmitter/receiver and the short range wireless radio transmitter/receiver; motion detection circuit. The battery power management circuit determines that the short range wireless radio transmitter/receiver is in communication with a short range wireless radio transmitter/receiver of the monitoring and communication control device. If the personal monitoring communication device is in communication with the monitoring and is communication control device, the global positioning system receiver and the cellular telephone radio transmitter/receiver are disabled.

If the personal monitoring communication device is not in communication with the monitoring and communication control device with the short range wireless radio transmitter/receiver, the global positioning system receiver and the cellular telephone radio transmitter/receiver are enabled. If the cellular telephone radio transmitter/receiver loses communication with the cellular telephone network, the global positioning system receiver is disabled and the cellular telephone radio transmitter/receiver is placed into a network search mode, in some embodiments and in a standby mode, in other embodiments. In various embodiments, if the cellular telephone radio transmitter/receiver has lost communication with the cellular telephone network, the emergency beacon is activated and transmitted on the short range wireless radio transmitter such that the personal monitoring communication device finder may be able to locate the personal monitoring communication device.

In some embodiments, the global positioning system receiver establishes a reference home location. If the short range wireless radio transmitter/receiver is not in contact with the monitoring and communication control device, the short range wireless radio transmitter/receiver is deactivated. When the personal monitoring communication device is brought within a relatively close distance of the reference home location, the short range wireless radio transmitter/receiver is activated to establish contact with the monitoring and communication control device.

In some embodiments, the motion detection circuit determines that the person coupled to the personal monitoring communication device is not in motion. If the person is not in motion, the global positioning system receiver is deactivated. When the motion detection circuit determines that the person is again in motion the global positioning system receiver is then reactivated.

If the battery sensing device indicates that the status of the battery has deteriorated to a first level, the battery management circuit commands that the personal is monitoring communication device reduce the location reporting frequency to the monitoring and communication control device and the cellular telephone radio transmitter/receiver and the global positioning system receiver be placed in a low-power standby mode for a longer period between the location reporting times. If the battery sensing device indicates that the status of the battery has deteriorated to a second level, the battery management circuit commands that the personal monitoring communication device place the cellular telephone radio transmitter/receiver in the low-power standby mode and the global positioning system receiver be disabled. The cellular telephone radio transmitter/receiver will be turned on when commanded through the cellular telephone network from the monitoring and communication control device.

In various embodiments, the battery power management circuit has a battery management finite state machine for implementing the functions of the battery power management circuit.

In some embodiments, the personal monitoring communication device has a tamper detection circuit to determine whether the personal monitoring communication device is coupled to the person being monitored. The tamper detection circuit has a capacitive sensor that senses the presence of the person being monitored and triggers an alert if the presence is not detected for a predetermined period of time.

BRIEF DESCRIPTION OF THE DRAWINGS

FIG. 14 is a chart of the functions of the states of the finite state machine of FIG. 13.

DETAILED DESCRIPTION OF THE INVENTION

Figure 1:
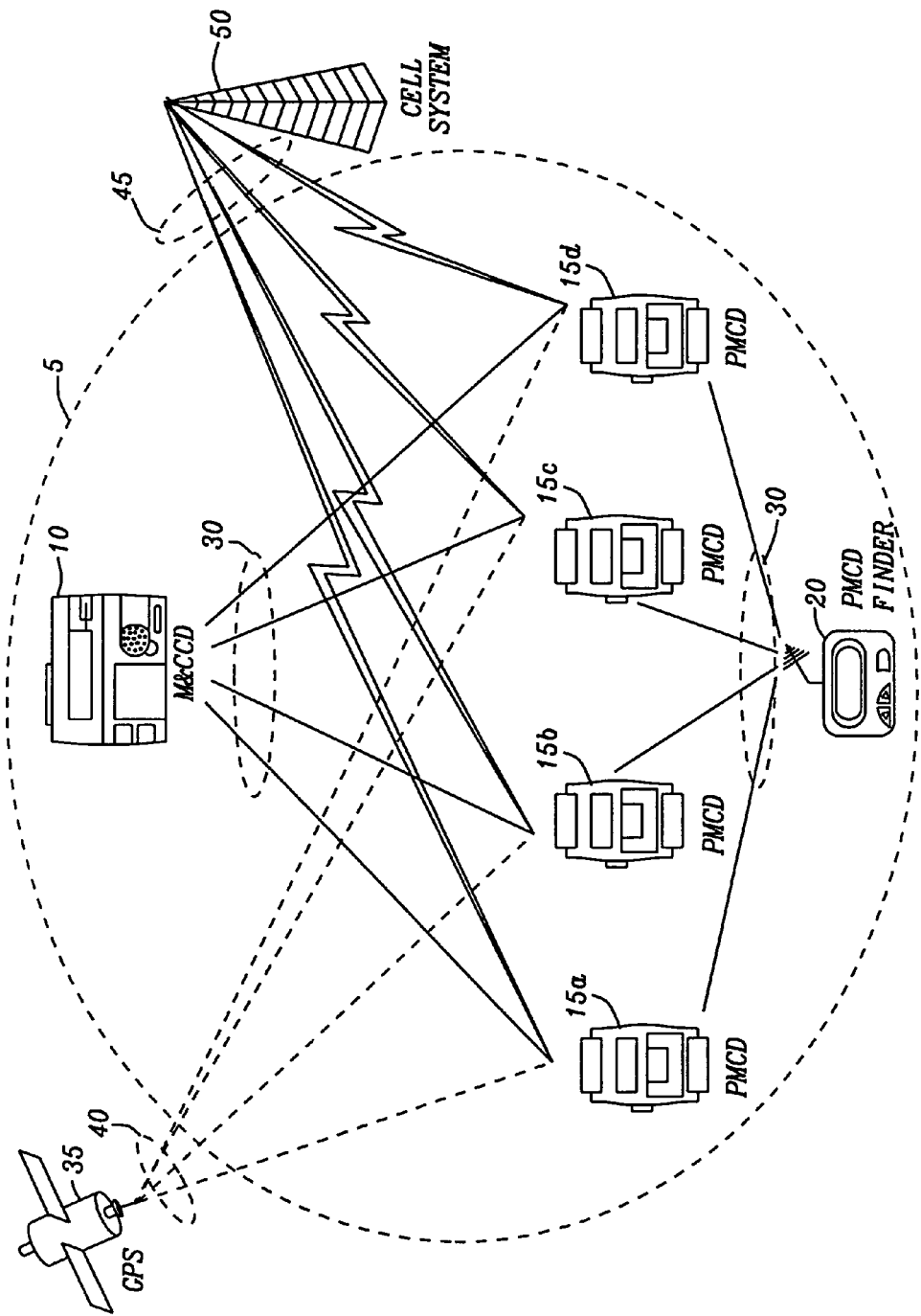
FIG. 1 is a diagram of an embodiment of a personal monitoring and communication system.

For this invention, personal monitoring communication device include personal emergency response systems, telehealth, and telemedicine systems. The personal emergency response systems allow users to send an alarm signal to a remote base station to alert caregivers to request assistance in an emergency. These normally consist of a mobile device wirelessly connected to a console, which communicates to caregivers via voice calls over standard analog telephone lines. The telehealth and telemedicine systems are for measurements and monitoring of users' health information, such as their vital signs. These are normally connected to remote caregivers using data, over the Internet or just using modems over analog telephone lines. The portable and/or wearable health management system such as watch or pendant as described in the 714 and 715 patent applications are personal monitoring communication devices 15a, 15b, 15c, and 15d as shown in FIG. 1. The console of the 714 and 715 patent applications is the monitoring and communication control device 10. In some embodiments of this invention, the personal monitoring communication devices 15a, 15b, 15c, and 15d and the monitoring and communication control device 10 further communicate with service communication devices such as lights and sound transducers (described in the 787 patent application). In the embodiments of this invention, the personal monitoring communication devices 15a, 15b, 15c, and 15d and the service communication devices are connected to the monitoring and communication control device 10 in a star or a mesh configuration.

FIG. 1 is a diagram of an embodiment of a communication network configured as a star network and a mesh network. FIG. 1 illustrates the star network 30 where a first type of communication device functions as the monitoring and communication control device 10, however in other embodiments, the wireless network 30 functions as a mesh network. The monitoring and communication control device 10 determines the network frequency channels within the frequency band on which the is node personal monitoring communication devices 15a, 15b, 15c, and 15d operate. Further, the monitoring and communication control device 10 determines a hopping sequence for the network frequency channels by which the node personal monitoring communication devices 15a, 15b, 15c, and 15d communicate. The monitoring and communication control devices 10 communicate with a second type of communication devices that is the personal monitoring communication devices 15a, 15b, 15c, and 15d through the wireless network 30. The wireless network 30 operates on frequency bands such as the unlicensed 2.4 GHz ISM (Industrial Scientific Medical) band.

The personal monitoring communication device 15a, 15b, 15c, and 15d is a personal monitoring communication device that in some embodiments allows a person to request and receive services from other devices communicating on the communication network 30. The personal monitoring communication device 15a, 15b, 15c, and 15d in various embodiments is a personal health management device for providing measurements and monitoring of users' health information, such as their vital signs and in an emergency, alerting emergency services and contact persons for the person coupled to the personal monitoring communication device 15a, 15b, 15c, and 15d. Further, the personal monitoring communication device 15a, 15b, 15c, and 15d allows the person to receive voice and data communications such voice conversations with other persons on the network or reminders for appointments or the taking of medication.

When any of the personal monitoring communication devices 15a, 15b, 15c, 15d or 35 are out of the range of the network 30 and must transmit a priority or emergency message, the personal monitoring communication device 15a, 15b, 15c, 15d communicates with a wide area wireless system such as a cellular system 50. The personal monitoring communication device 15a, 15b, 15c, 15d or 35 attempts to reestablish communication with the monitoring and communication control device 10 a number of times and then activates the cellular communication to communicate the emergency or priority message to the monitoring and communication control device 10 or other designated destination for the message.

In various embodiments, the personal monitoring communication devices is 15a, 15b, 15c, and 15d have a global positioning system receiver that determines a location based on receiving positioning signals 40 from a global positioning system 35. In some embodiments, the personal monitoring communication devices 15a, 15b, 15c, and 15d have an indoor dead reckoning circuit for determining a location of the person coupled to the personal monitoring communication devices 15a, 15b, 15c, and 15d, when in location at which the global positioning system is not functional. In various embodiments, the personal monitoring communication devices 15a, 15b, 15c, and 15d include a motion detector that determines if the person coupled to the personal monitoring communication devices 15a, 15b, 15c, and 15d is moving, is stationary, or has fallen. The motion detector provides data such that a dead reckoning circuit can calculate an estimate of the distance and direction the person has traveled when the person is moving.

In some embodiments, the personal monitoring and communication system 5 has a personal monitoring communication device finder 20 for determining a location of the person coupled to the personal monitoring communication device 15a, 15b, 15c, and 15d. The personal monitoring communication devices 15a, 15b, 15c, and 15d each have a "panic button function" that activates an emergency beacon that is transmitted through the wireless network 30 to the monitoring and communication control device 10 and to the personal monitoring communication device finder 20. The signals transmitted to the personal monitoring communication device finder 20 on the wireless network 30 have the emergency beacon message format and a slow hopping frequency channel sequence that is described hereinafter.

Figure 2:
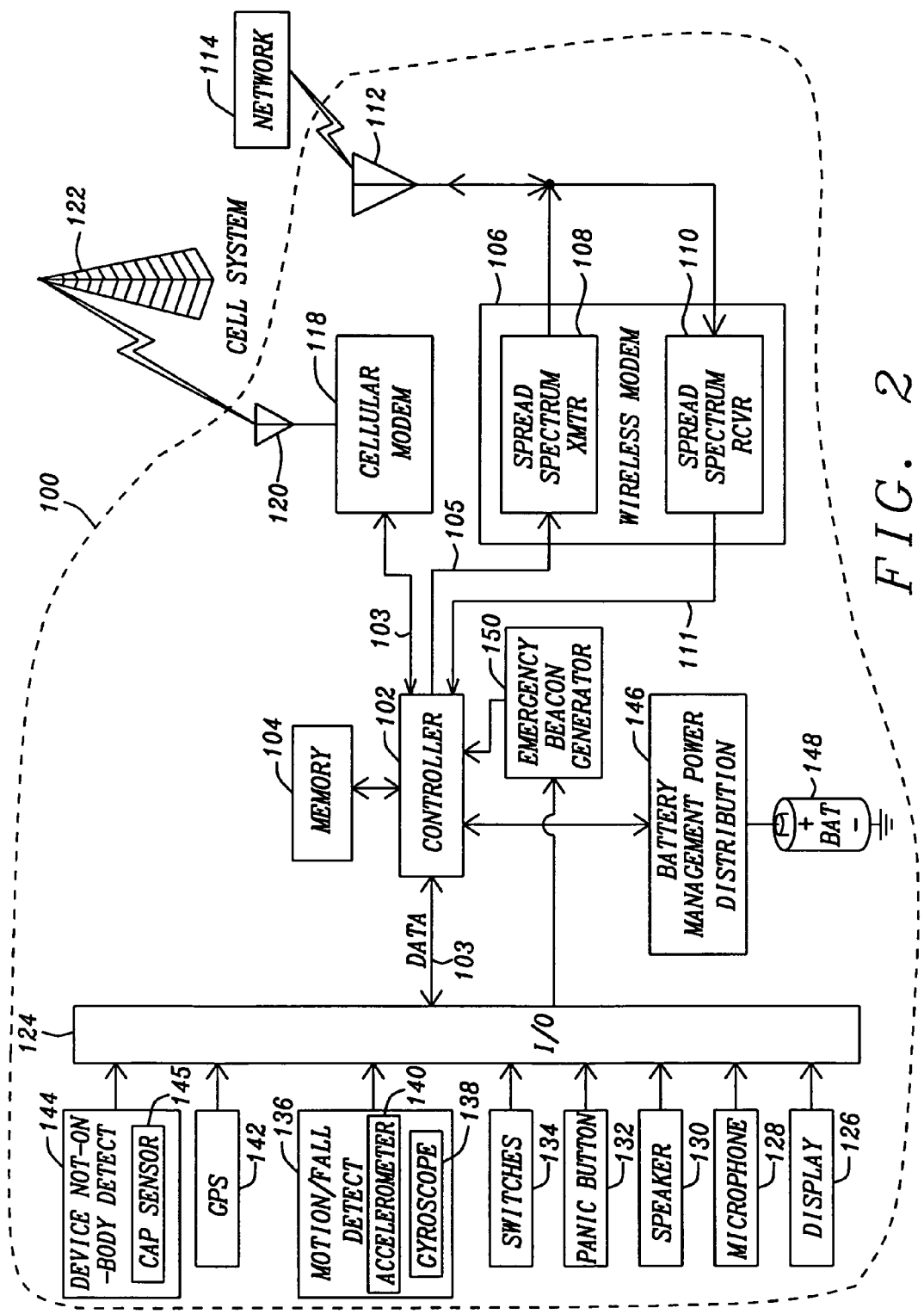
FIG. 2 is a block diagram of an embodiment of a personal monitoring communication device of a personal monitoring and communication system.

FIG. 2 is a block diagram of a personal monitoring communication device 100 as shown as the personal monitoring communication devices 15a, 15b, 15c, and 15d of the personal monitoring and communication system 5 in FIG. 1.

The communication device 100 has a controller 102 connected to a short range local area wireless network modem 106 with the transmission bus 105 and the receiving bus 111 and a wide area wireless modem 118 such as a cellular modem with the cellular bus 103. The controller 102 is connected to a memory 104. The memory 104 retains the computer executable code that, when executed by the controller 102, provides the processes for controlling the operation of the personal monitoring communication device 100. In various embodiments, the personal monitoring communication device 100 has a battery 148 and a battery management circuit 146. The battery management circuit will implement processes for conserving energy used from the battery 148. Therefore, the controller 102 is connected to a battery management circuit 146 that will provide the timing for the activation and deactivation of the functions of the communication device 100.

The controller 102 is connected to an Input/Output Interface (I/O) 124 for providing data and control information 103 to the controller 102. The I/O Interface 124 provides the buffering and signal conditioning for signals from I/O devices included in the personal monitoring communication device 100. The I/O devices include such devices as a display 126 for showing alphanumeric and graphic information (including current time), a microphone 128 and a speaker 130 for voice communication, a panic-button switch 132. The switches 130 provide a user interface to support functions including emergency alert one-touch access to 911 services, a favorite help button for contacting personal care and significant personnel, one-touch connection to other devices in the network such as the monitoring and communication control device 10 of FIG. 1, and commanding services from the service devices (not shown). Additional interface devices include a motion/fall detector 136 which includes a gyroscope 138 and a three axis accelerometer 140 for determining if the person coupled to the personal monitoring communication device 100 is moving, has not moved for a period of time, or has fallen. If the person is moving the gyroscope 138 and the three axis accelerometer 140 provide a direction vector and an acceleration vector used for indoor dead reckoning. A global positioning system (GPS) unit 142 is provided for determining the location of the personal monitoring communication device 100. Other sensors (not shown) such as health monitoring devices may be included in the personal monitoring communication device 100 and be in keeping with the intent of this invention.

The I/O devices, when activated, transfer data to the controller 102 which retrieves the computer code to execute an appropriate process indicated by the device activated. When communication to the monitoring and communication control device 10 is indicated, the controller 102 activates the spread spectrum receiver 110 of the wireless modem 106 by transmitting a normal communication message to determine that the communication device 100 is in communication with at least the monitoring and communication control device 10 of FIG. 1. If the communication device is in communication with at least the monitoring and communication control device 10, the normal communication message to the controller indicating that at least the monitoring and communication control device 10 is communicating. The spread spectrum transmitter 108 is then activated for communicating data with the normal communication messages through the short range local area wireless network 114. For instance if a switch 134 indicating that a light switch is be activated to turn on a light, the personal monitoring communication device 100 transmits a command to the monitoring and communication control device 10 and then another communication device connected to the light. The other communication device receives the command and activates the light. The spread spectrum transmitter 108 and the spread spectrum receiver 110 are connected to an antenna 112 that radiates radio frequency signals to the monitoring and communication control device 10 on the short range local area wireless network 114.

If the personal monitoring communication device 100 is not able to join or resynchronize with the short range local area wireless network 114 or an emergency has occurred, the controller 102 activates the cellular modem 118 and communicates through the antenna 120 to the wide area wireless system or cellular system 122. The cellular communication is generally reserved for emergency or urgent messages or when the personal monitoring communication device 100 is beyond the range of the wireless network 114.

If the panic button 132 or the monitoring and communication control device 10 transmits a command to activate an emergency beacon, the emergency beacon generator 150 creates a long pseudorandom bit sequence and a slow frequency hopping sequence as an emergency beacon message that is transferred to the controller 102 for transfer to the wireless modem for transmission through the antenna 112 to the short range local area wireless network 114. The emergency beacon is received by the personal monitoring communication device finder 20 of FIG. 1 such that the personal monitoring communication device finder 20 can locate the personal monitoring communication device 100.

A battery 148 provides the power for the personal monitoring communication device 100. The battery 148 is connected to a battery management and power distribution circuit 146. The battery management and power distribution circuit 146 monitors the activity of the circuits of the personal monitoring communication device 100 and controls the distribution of power to the circuits of the personal monitoring communication device 100 to appropriately activate and deactivate the circuits. The activation and deactivation minimizes the using of power from the battery 148 to extend the life of the battery 148.

Figure 3:
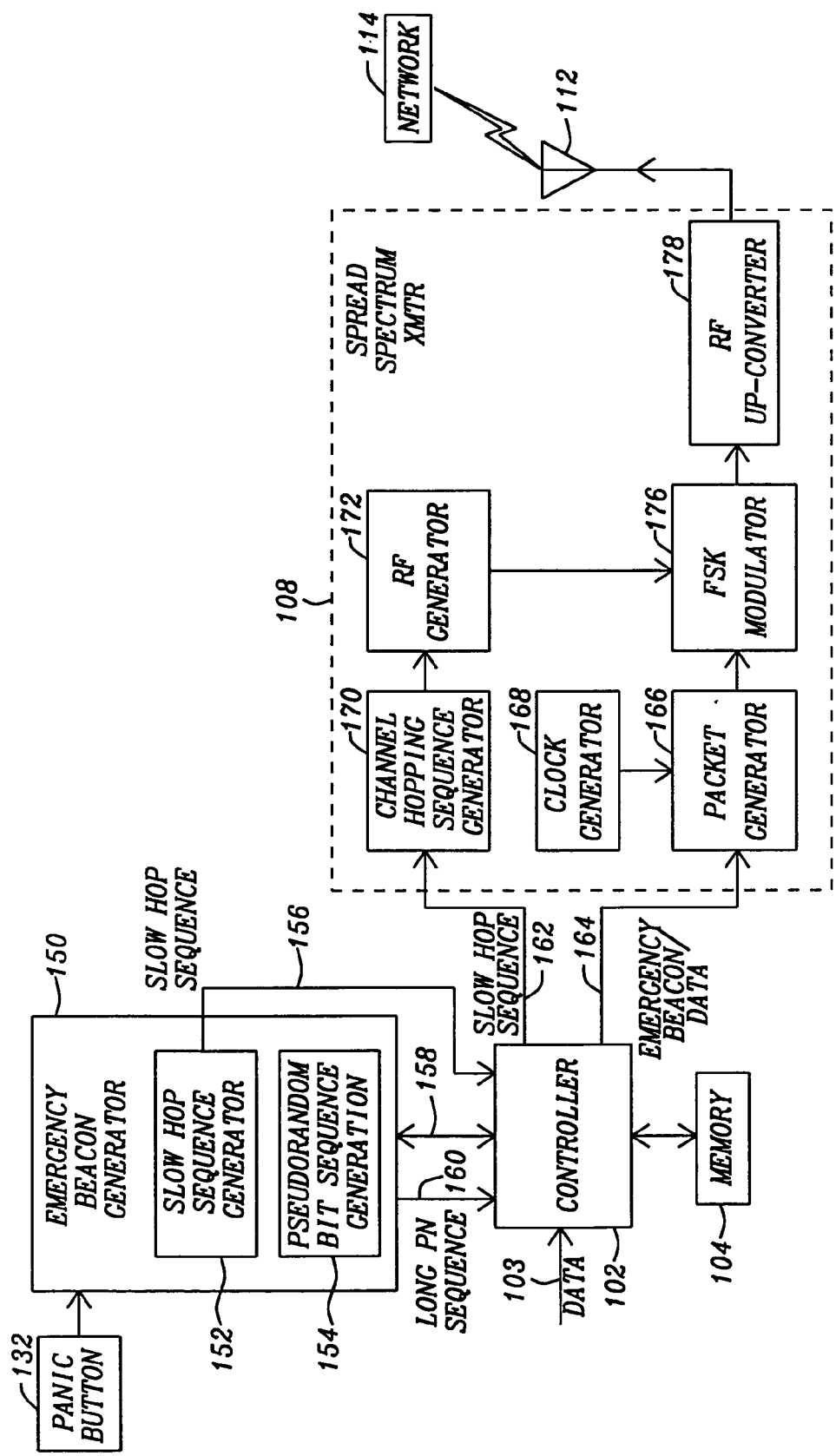
FIG. 3 is a block diagram of an embodiment of the transmitter of the personal monitoring communication device of FIG. 2 illustrating the emergency beacon.

FIG. 3 is a block diagram of the transmitter of the personal monitoring communication device of FIG. 2 illustrating the emergency beacon. The personal monitoring communication device 100 is a dual-mode device that operates in a normal mode and as an emergency beacon. Under the normal mode, the personal monitoring communication device 100 communicates with the normal communication message structure supports a wireless protocol as described in the 787 patent application. The personal monitoring communication device 100 supports voice and data communications with the monitoring and communication control device 10. The personal monitoring communication device 100 may be used for making voice calls including personal emergency response systems (PERS) calls. The personal monitoring communication device 100 place the call via the short range local area wireless network modem 106 first if it is available or place the call using the wide area wireless modem 118 to the wide area wireless system or cellular system 122 if the short range local area wireless network 114 is not available.

If the person being monitored activates the panic button 132 or the monitoring and communication control device 10 commands that the emergency beacon be activated, the personal monitoring communication device 100 is operated as the emergency beacon. In the emergency beacon mode, the personal monitoring communication device 100 uses the same physical layer or circuits within the spread spectrum transmitter 108 to transmit a pseudorandom (PN) sequence of arbitrarily long duration, with bit repetition by a factor.

The repetition factor is maximized for ease of demodulation and detection at the receiver, but its maximum value is usually governed by the minimum signal bandwidth as per regulatory requirements such as FCC Part 15.247. The product of (bit period×repetition factor×PN length)=dwell time, which is usually regulated also by a maximum, for example, 0.4 seconds under FCC Part 15. The choice of repetition factor with PN length allows all these regulations to be met while minimizing receiver complexity. In a practical example, the normal mode bit rate=1 Mbps, bit repetition period=10, arbitrarily long pseudorandom bit sequence length=1023. The dwell time is then calculated to be 10.23 ms.

For interference avoidance, the long arbitrarily long pseudorandom bit sequence pattern is repeated at different frequencies determined by a slow hopping sequence. The slow hopping sequence differs from the fast hopping sequence used in normal mode in that firstly it uses fewer frequencies, and secondly the duration of each hop is equal to the duration of the arbitrarily long pseudorandom bit sequence pattern.

When the personal monitoring communication device 100 is transferred from the normal mode to the emergency beacon mode, the emergency beacon generator 150 produces the sequence of channel frequencies 156 that are transferred to the controller 103. The slow hopping sequence is transferred from the controller 103 to the channel hopping sequence generator 170 which instructs the radio frequency generator 170 to generate the carrier frequency signals for each of the channels of the slow channel hopping sequence.

Figure 4:
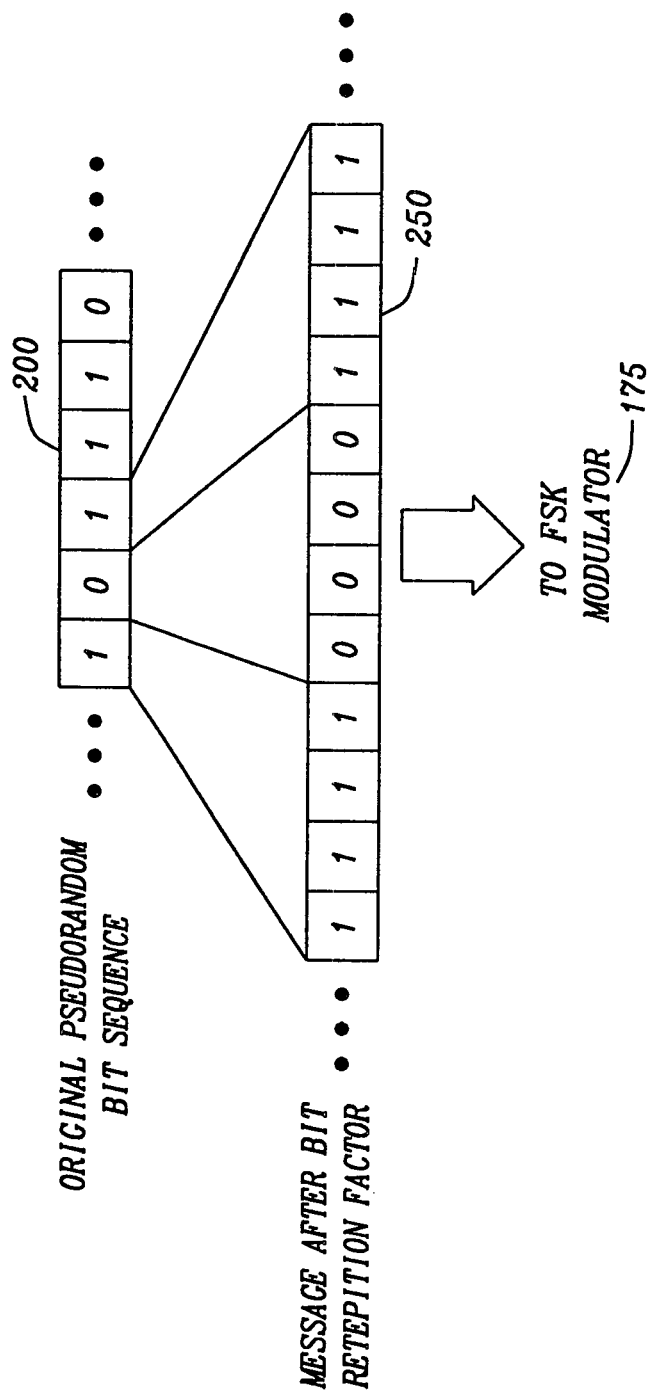
FIG. 4 is a diagram of an embodiment of long pseudorandom bit sequence incorporating a repetition factor for reducing a bit rate of an emergency beacon message as transmitted by the personal monitoring communication device of FIG. 2.

The pseudorandom bit sequence generator 154 generates the arbitrarily long pseudorandom bit sequence pattern 160 that is transferred to the controller 102. The controller 102 transfers the arbitrarily long pseudorandom bit sequence pattern 164 as the emergency beacon data to the packet generator 166. The clock generator 168 provides the necessary timing signals for developing the message packets that are transferred to the frequency shift keying modulator 176. The frequency shift keying modulator 176 modulates the radio frequency carriers and transfers the modulated signal to the radio frequency up-converter 178. The radio frequency up-converter 178 then shifts the modulated signal to the appropriate frequencies of the radio frequency band that the personal monitoring communication device 100 operates. The up-converted signal is then transferred to the antenna 112 for transmission on the short range local area wireless network 114. The emergency beacon is the message structure of the normal mode as described in the 787 patent application, except it is simplified to being just the pseudorandom bit sequence transmitted for a single time with a bit rate reduced by the repetition factor. FIG. 4 is a diagram of a long pseudorandom bit sequence incorporating a repetition factor for reducing a bit rate of an emergency beacon message generated by the emergency beacon circuitry 150 of FIG. 3, as transmitted by the personal monitoring communication device of FIG. 2. The long pseudorandom bit sequence 235 consists of a pseudo-random random bit sequence determined by the pseudorandom bit sequence generator 154. The long pseudorandom bit sequence 235 is then expanded by the bit repetition factor to create the long pseudorandom message 250 that is received by the controller 102 that is transferred as the emergency beacon to the packet generator 166 and directly to the frequency shift keying modulator 176. The emergency beacon is then transferred to the RF up-converter 178 and thus to the antenna 112 for transmission to the network 114. The bit repetition factor permits the use the controller 102 and the spread spectrum transmitter 108, while effectively reducing the bit rate by the repetition factor. It is independent of the pseudorandom sequence as can be seen in the equation for the dwell time above. The purpose for reducing the bit rate is to increase the energy per bit, and thus the signal-to-noise ratio at the receiver.

Figure 5:
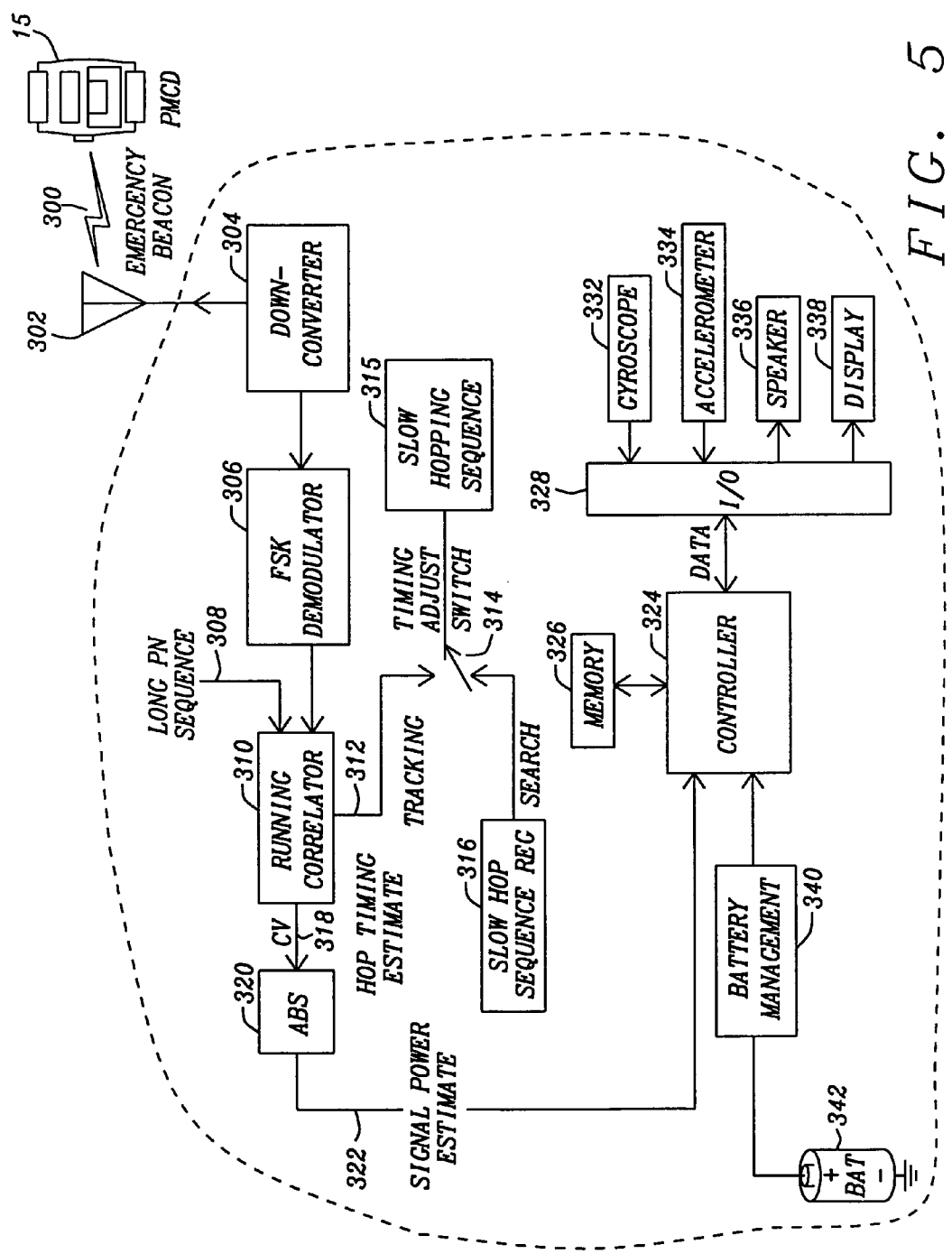
FIG. 5 is a block diagram of an embodiment of a personal monitoring communication device finder.

FIG. 5 is a block diagram of a personal monitoring communication device finder 20 of FIG. 1. A personal monitoring communication device 15 transmits a modulated emergency beacon 300 that is received by the antenna 302 and transferred to a conventional frequency-hopping receiver. The frequency of the emergency beacon 300 is applied to the down-converter 304 and down-converted to an intermediate frequency that is transferred to the frequency shift keying demodulator 306. The frequency shift keying demodulator 306 extracts the arbitrarily long pseudorandom bit sequence 235 of FIG. 4 and transfers it to the running correlator 310. The running-correlator 310 performs a correlation operation the received arbitrarily long pseudorandom bit sequence 235 with a local replica of the baseband arbitrarily long pseudorandom bit sequence 235. The local replica pseudorandom sequence is generated based on prior knowledge of a seed for generating the long pseudorandom bit sequence 235 of a personal monitoring communication device 15a, 15b, 15c, and 15d that is not accounted for and may be transmitting an emergency beacon. The unique long pseudorandom bit sequence 235 code is generated based on an identification code of the unaccounted for personal monitoring communication device 15a, 15b, 15c, and 15d. In some embodiments, the long pseudorandom bit sequence 235 code is generated as sequences of bits having a length m. In other embodiments, a maximal-length shift register is initialized by a seed that is either directly the identification code of the personal monitoring communication device 15a, 15b, 15c, and 15d, or in other embodiments, the seed is a function of the identification code of the personal monitoring communication device 15a, 15b, 15c, and 15d.

The running correlator 310 operates at a low multiple of the frequency shift keying symbol rate. The output of the running correlator 310 is determined as: $\Sigma[x(n)*r(n)]$, where $x(n)$ =local replica of the arbitrarily long pseudorandom bit sequence 235, $r(n)$=received arbitrarily long pseudorandom bit sequence 235. The summation is performed over the time duration of the arbitrarily long pseudorandom bit sequence 235. The running correlator 310 operates once every received signal sample. Thus the sampling rate is a low multiple (e.g. =8) of the bit rate. This low multiple of the bit rate and minimizing the bit rate helps in reducing the computation by the running correlator 310. As an example, using the parameters previously shown for the normal operation, the running correlator 310 would require a bit sequence that is the product of the repetition rate of the repetition rate of the long pseudorandom bit sequence 235 code, the bit rate in bits per second, and the sequence length. For a repetition rate of 8, a bit is rate of 100 Kbps, and a length of the long pseudorandom bit sequence 235 code of 1023 bits, the running correlator requires 818.4M multiply/add operations per second. The running correlator 310, in various embodiments, is a program process incorporated in a digital signal processing component of the controller circuit 324. The performance level required is achievable with present digital signal processing components costing approximately $10.00.

At the initiation of the personal monitoring communication device finder 20, the timing adjustment switch 314 is set to connect the slow hop sequence register 316. The slow hop sequence register 316 provides an initial hop sequence to the slow hopping sequence generator 315 to provide the correct channel frequency to the down converter 304 to extract the base band frequency from the received emergency beacon signal 300. The running correlator 310 derives a hop timing estimate 312 by searching for peak values of the output of the running correlator 310 that are repeated at every hop sequence period. The timing adjustment switch 314 is then changed to transfer the hop timing estimate to the slow hopping sequence generator 315 to adjust the hopping sequence to accurately acquire the received emergency beacon 300.

The output 318 of the running correlator 310 is an input to the absolute value circuit 320 that provides an absolute value of the correlator output value 318 of the running correlator 310. The absolute value of the correlator output value 318 of the running correlator 310 is essentially an estimated received signal power value 322 that is applied to the controller 324. The controller 324 then determines an estimate of the distance of the personal monitoring communication device 15 from the monitoring and communication control device 10 based on the estimated received signal power value 322 and the knowledge of the personal monitoring communication device 15 transmit power, the gain of the receiver of the personal monitoring communication device finder 20, and the typical propagation path loss models. The estimated received signal power value 322 (Pr) is determined as the peak absolute value of the output of the running correlator 310 divided by a constant (K). The constant (K) is a constant of proportionality. This means that the output of the running correlator 310 is linearly proportional to the estimated received signal power value 322 (Pr). The constant (K) is determined by the total receiver gain and the integration time period over which the running correlator 310 operates. The estimated received signal power value 322 is related to the distance by the formula:

$$Pr=Pt+Gr-n*10 \log(d)+C \qquad \text{Eq. 1}$$

Where:
Pr is the received power in dBm,
Pt is the transmit power in dBm,
Gr is the total receiver gain in dB,
n is the path loss coefficient (normally between 2 and 3) and is proportional to the distance (10 log(d)) from the personal monitoring communication devices 15 and the monitoring and communication control device 10 in dB, and
C is a constant determined by the signal frequency and is assumed to be $20 \log(4\pi/3\times10^8)$ dB.

It can be shown that the distance from the personal monitoring communication devices 15 and the monitoring and communication control device 10 can be calculated by the controller 324.

The direction of arrival of the emergency beacon message 200 is determined by one or more directional antennas 302, and thus the personal monitoring communication device finder 20 is able to give a relative location estimate of the personal monitoring communication devices 15.

To determine the direction of arrival, the antenna 300 as shown must be multiple antennas configured to have their receive pattern overlapped and covering all 360 degrees surrounding the personal monitoring communication device finder 20. The direction of arrival using standard techniques such as those described in Chapter 7 in F. B. Gross, *Smart*

*Antennas for Wireless Communications*, McGraw Hill, Inc, New York, N.Y., 2005. With a single antenna 300, the direction of arrival is determined by rotating the antenna 300 manually and finding the peak estimated signal power value 322.

The accuracy of the personal monitoring communication device finder 20 has an accuracy that depends on the environment. If the fixed path loss coefficient "n" in the above equation is chosen to be, for example, 2.5, then in very open space the actual value for the path loss coefficient "n" is closer to 2, in which case the error can be shown to about three times too short. Alternately, if the personal monitoring communication device finder 20 is indoors, the actual path loss coefficient "n" is closer to 3. Then the error can be shown to be about three times too far. The range of the transmitter of the personal monitoring communication device finder 20 in free-space with no interference can be very long—up to several miles if using high-gain directional antennas. In practice, because the 2.4 GHz ISM band is crowded, it will be limited by interference to around 0.5 mile using a consumer quality receiver. The personal monitoring and communication system with the personal monitoring communication device finder 20 and the personal monitoring communication device 15 functions within the last mile as a backup solution when the GPS unit 35 and/or the cellular system 50 of FIG. 1 is not available, such as inside a shopping mall.

Figure 6:
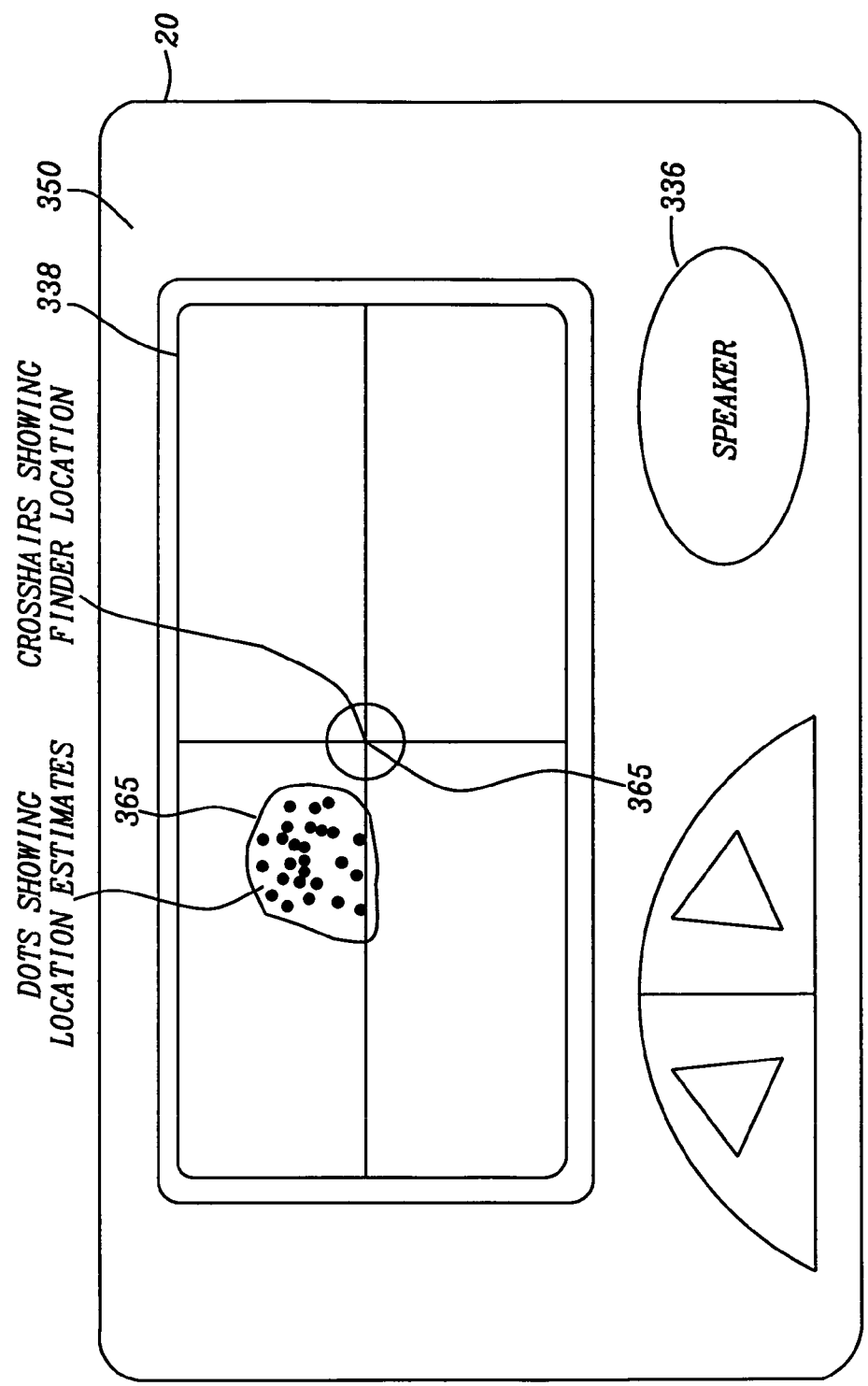
FIG. 6 is a diagram of an embodiment of a front panel of the personal monitoring communication device finder of FIG. 4.

FIG. 6 is a diagram of a front panel 350 of the personal monitoring communication device finder 20 of FIG. 4. The personal monitoring communication device finder 20 may indicate the distance estimate by visual or audible means, and indicate the direction of arrival of the signal. The front panel 350 of personal monitoring communication device finder 20, in some embodiments, has a display 338 showing location of the personal monitoring communication device finder 20 and the estimated direction and distance to the location 360 of the personal monitoring communication device 15 on a map on the display. In other embodiments, the direction and distance to the personal monitoring communication device 15 is an audible indication broadcast by a speaker 336. The display 338 will display other information.

The personal monitoring communication device finder 20, in other embodiments, incorporates a gyroscope 332 and accelerometer 334 of FIG. 4, which allows the relative motion of the personal monitoring communication device finder 20 to be known. The display 338 is updated according to the motion and location of the is personal monitoring communication device finder 20. Location estimates are constantly generated as long as the emergency beacon signal 300 is received. Each location estimate displayed as one dot 365 on the map of the display 338. The intensity of each of the dots 365 is reduced progressively over time from the sample. The concentration and intensity of dots 365 give a easily-recognizable representation of the likelihood of the location.

Returning to FIG. 5, the personal monitoring communication device finder 20 includes a battery management circuit 342 and a battery 344. The operation of the personal monitoring communication device finder 20 with the objective of minimizing power consumption and hence increasing battery life, while maintaining location determining performance to be virtually unchanged. The battery level status determined by the battery management circuit 342 is used to prolong the battery life of the personal monitoring communication device finder 20 with graceful degradation of location finding performance. The location determining rate may be reduced gradually as long as possible.

In various embodiments of the personal monitoring communication device finder 20, the controller 324 performs the function of the running correlator 310, the absolute value circuit 320, and the battery management circuit 340. The memory 326 is the repository for the program processes executed by the controller 324 for performing the functions. The signals from the gyroscope 332, the accelerometer 334 are transferred to the I/O interface circuit 328 and to the controller 324 for processing. The signals to be transferred to the speaker 336 and the display 338 are passed from the controller 324 through the I/O interface circuit 328.

In some embodiments, the monitoring and communication control device 10 incorporates the functions of personal monitoring communication device finder 20 together in one physical unit. The monitoring and communication control device 10 is used in normal operation as a stationary device in a fixed home location, but also in the event that the personal monitoring communication device 15 needs to be located, the monitoring and communication control device 10 can be made mobile and assumes the is functions of the personal monitoring communication device finder 20 to locate the personal monitoring communication device 15.

Figure 7:
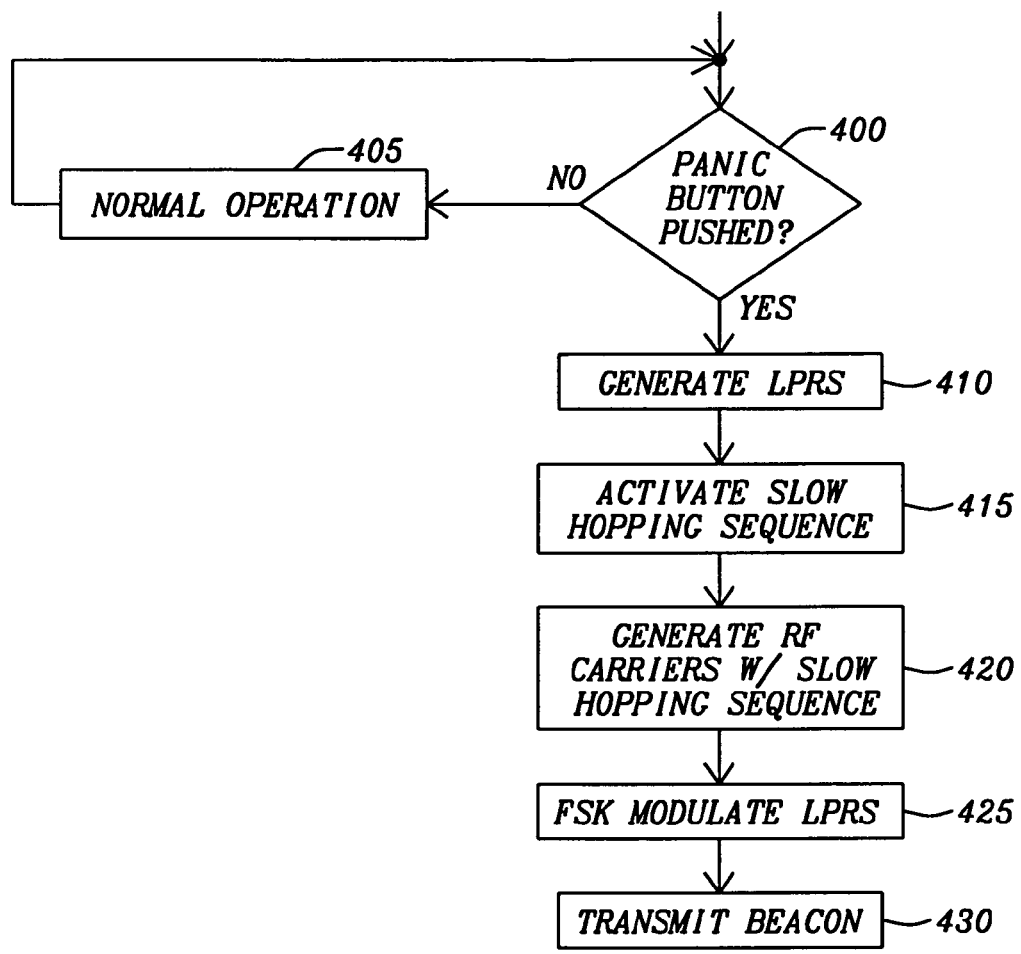
FIG. 7 is a flowchart of an embodiment of a method for generating the emergency beacon message transmitted by the personal monitoring communication device of FIG. 2.

FIG. 7 is a flowchart of a method for generating the emergency beacon message 200 of FIG. 4 transmitted by the personal monitoring communication device 100 of FIG. 2. Referring to FIGS. 2 and 7, the method for generating the emergency beacon message starts by determining (Box 400) if the panic-button switch 132 has been pushed or alternately the monitoring and communication control device 10 has commanded the activation of the emergency beacon 200. If the panic-button switch 132 has not been pushed or the monitoring and communication control device 10 has not commanded the activation of the emergency beacon 200, the personal monitoring communication device 15 functions in a normal operation mode (Box 405). If the panic-button switch 132 has been pushed or the monitoring and communication control device 10 has commanded the activation of the emergency beacon 200, the emergency beacon generator 150 generates (Box 410) the arbitrarily long pseudorandom bit sequence. The emergency beacon generator 150 activates (Box 415) the slow hopping channel sequence. The channel hopping sequence generator 170 activates the RF generator 172 to generate (Box 420) the channel carrier frequencies. The frequency shift keying modulator 176 modulates (Box 425) the carrier frequencies with the arbitrarily long pseudorandom bit sequence and the emergency beacon is transmitted (Box 430)

Figure 8:
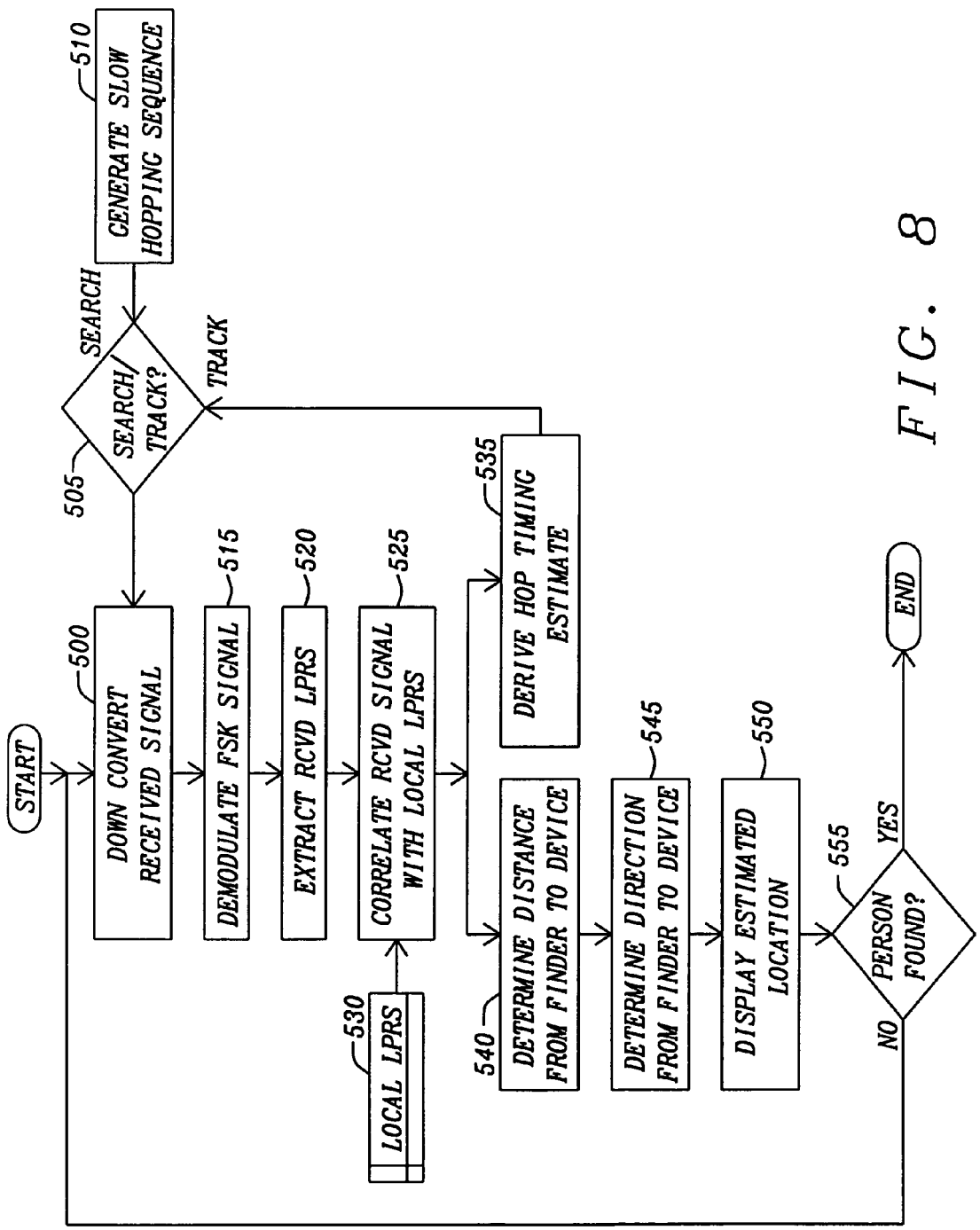
FIG. 8 is flowchart of an embodiment of a method for determining a location of a person coupled to a personal monitoring communication device by the personal monitoring communication device finder.

FIG. 8 is flowchart of an embodiment of a method for determining a location of a person coupled to a personal monitoring communication device 100 by the personal monitoring communication device finder 20. The method for locating the personal monitoring communication device 100 that has had its emergency beacon activated begins with down-converting (Box 500) the received frequency hopping emergency beacon 300 with a signal developed by a generated (Box 510) slow hopping channel frequency sequence that is selected (Box 505) by the timing adjust switch 314. The received frequency shift keying signal is demodulated (Box 515) and the arbitrarily long pseudorandom bit sequence is extracted (Box 520). The received arbitrarily long pseudorandom bit sequence is correlated (Box 525) with the local version 530 of the is arbitrarily long pseudorandom bit sequence. The local version 530 of the arbitrarily long pseudorandom bit sequence is generated based on prior knowledge of a seed for generating the long pseudorandom bit sequence 235 of a personal monitoring communication device 15a, 15b, 15c, and 15d that is not accounted for and may be transmitting an emergency beacon. The unique long pseudorandom bit sequence 235 code is generated based on an identification code of the unaccounted for personal monitoring communication device 15a, 15b, 15c, and 15d. In some embodiments, the long pseudorandom bit sequence 235 code is generated as sequences of bits having a length m. In other embodiments, a maximal-length shift register is initialized by a seed that is either directly the identification code of the personal monitoring communication device 15a, 15b, 15c, and 15d, or in other embodiments, the seed is a function of the identification code of the personal monitoring communication device 15a, 15b, 15c, and 15d.

A hop timing estimate is derived (Box 535) from the correlated received arbitrarily long pseudorandom bit sequence. The hop timing estimate is selected (Box 505) by the timing adjust switch 314 for adjusting the slow hopping sequence to align with the received emergency beacon signal 300. At this same time, the absolute value of the correlated received arbitrarily long pseudorandom bit sequence provides an indicator of the peak power (Pr) of the receiver. From Eq. 1 above, the distance of the personal monitoring communication device 15 to the personal monitoring communication device finder 20 is determined (Box 540). The direction of the personal monitoring communication device 100 with the activated emergency beacon is determined (Box 545) as described above. The estimated location of the personal monitoring communication device 100 with the activated emergency beacon is displayed (Box 550) as described in FIG. 6. It is determined (Box 555) if the personal monitoring communication device 15 is found. If not, the process is repeated with the next sampling. If the personal monitoring communication device 100 is found the process is ended and the personal monitoring communication device finder 20 is deactivated.

Figure 9:
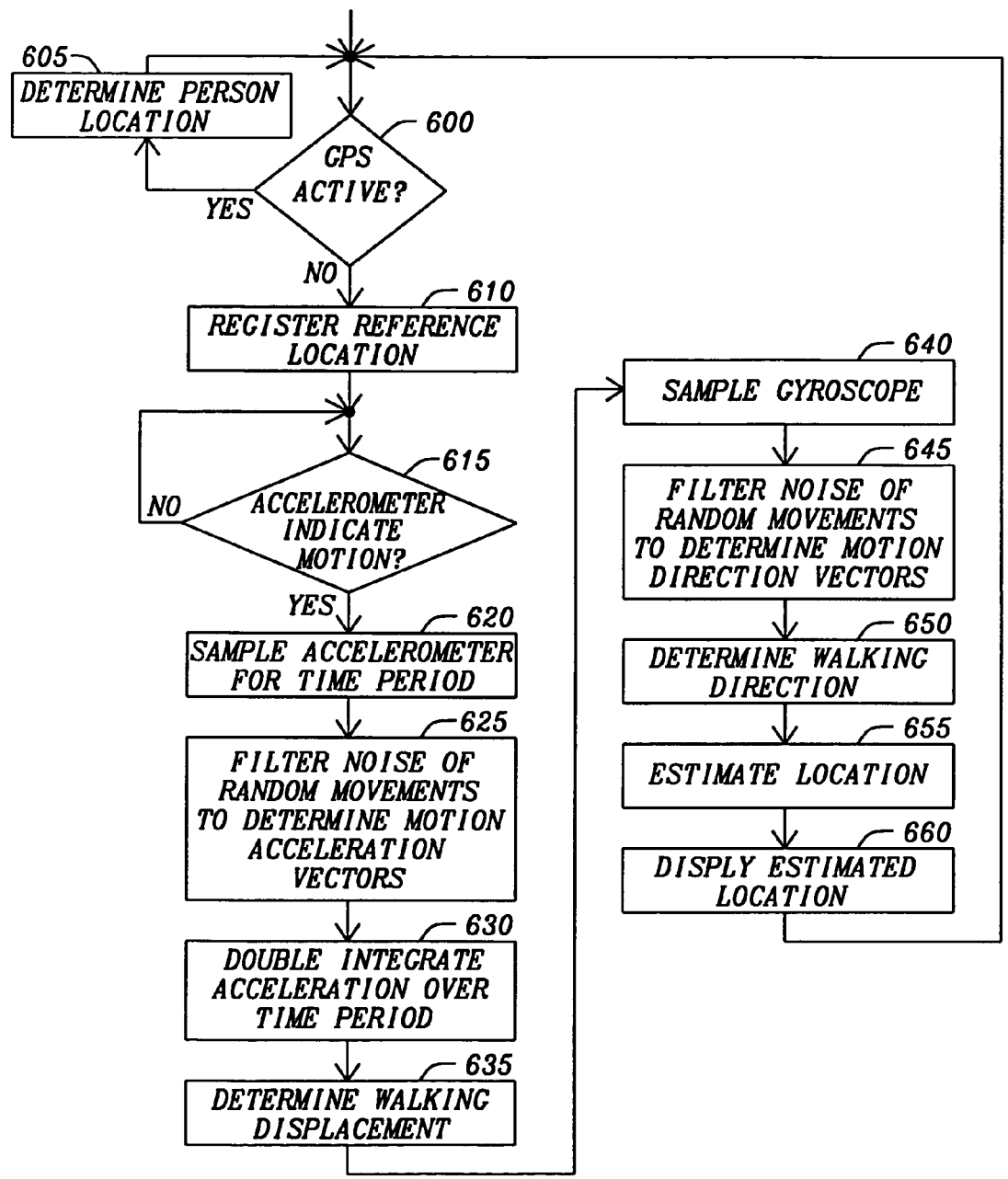
FIG. 9 is a flowchart of an embodiment of a method for indoor dead reckoning by a personal monitoring communication device of FIG. 2.

FIG. 9 is a flowchart of a method for indoor dead reckoning by a personal monitoring communication device 100 of FIG. 2. Referring to FIGS. 2 and 9, the GPS unit 142 may not function, if the person wearing the personal monitoring communication device 100 is inside a building or in an area where the reception of the GPS signals is not receivable such as narrow streets with large building of large cities. An estimate of the location tracking of the personal monitoring communication device 100 may be determined using dead-reckoning or autonomous relative location tracking methods based on inertial navigation principles such at those described in "Basic Inertial Navigation", Stovall, Naval Air Warfare Center, Report No. NAWCWPNS™ 8128, September 1997. The gyroscope 138 and three axis accelerometer 140 are used to estimate motion from a reference point, as set by the last available GPS location. The relative locations can be reported in a similar manner as GPS location. The method for indoor dead reckoning begins with determining (Box 600) that the GPS unit 142 is active. If the GPS unit 142 is active, the person's location is determined (Box 605). If the GPS unit 142 is inactive, the reference location is registered (Box 610) as the last location determined by the GPS unit 142. The accelerometer 140 is examined (Box 615) to determine if the personal monitoring communication device 100 is in motion. If the accelerometer 140 is not in motion, the three axis accelerometer 140 is examined (Box 615) until it is determined to be in motion. The data from the accelerometer 140 is read (Box 620) for a time period. The noise of random movements of the person wearing the personal monitoring communication device 100 is filtered (Box 625) to determine the movement acceleration vectors.

All motions are measured accurately by the gyroscope 138 and the three-axis accelerometer 140. The small scale wrist movements or large scale full body walking result in displacement vectors that form the path that the personal monitoring communication device 100 has traveled. The gyroscope 138 and three-axis accelerometer 140 have the resolution, dynamic range, sampling frequency and accuracy for collecting accurate data detailing the movement of the dead reckoning circuit. Given accurate data, simple averaging and low-pass filtering (Box 625) of the displacement data removes small scale changes (high frequency) and extract only the large scale changes (low frequency) for location determination.

The data from the three axis accelerometer 140 is double integrated (Box 630) to determine a displacement vector of the personal monitoring communication device 100 over the time period. From the displacement vector, the distance from the reference location is determined (Box 635).

The gyroscope 138 data is sampled (Box 640) to determine a motion direction vector. The motion direction vector is filtered (Box 645) to remove the random motions such as a person waving their arms. The walking direction vector is determined (Box 650). From the direction vector and the distance from the reference location, the location of the person wearing the personal monitoring communication device 100 is estimated (Box 655). The estimated location is transmitted to the monitoring and communication control device 10 for display (Box 660).

Figure 10:
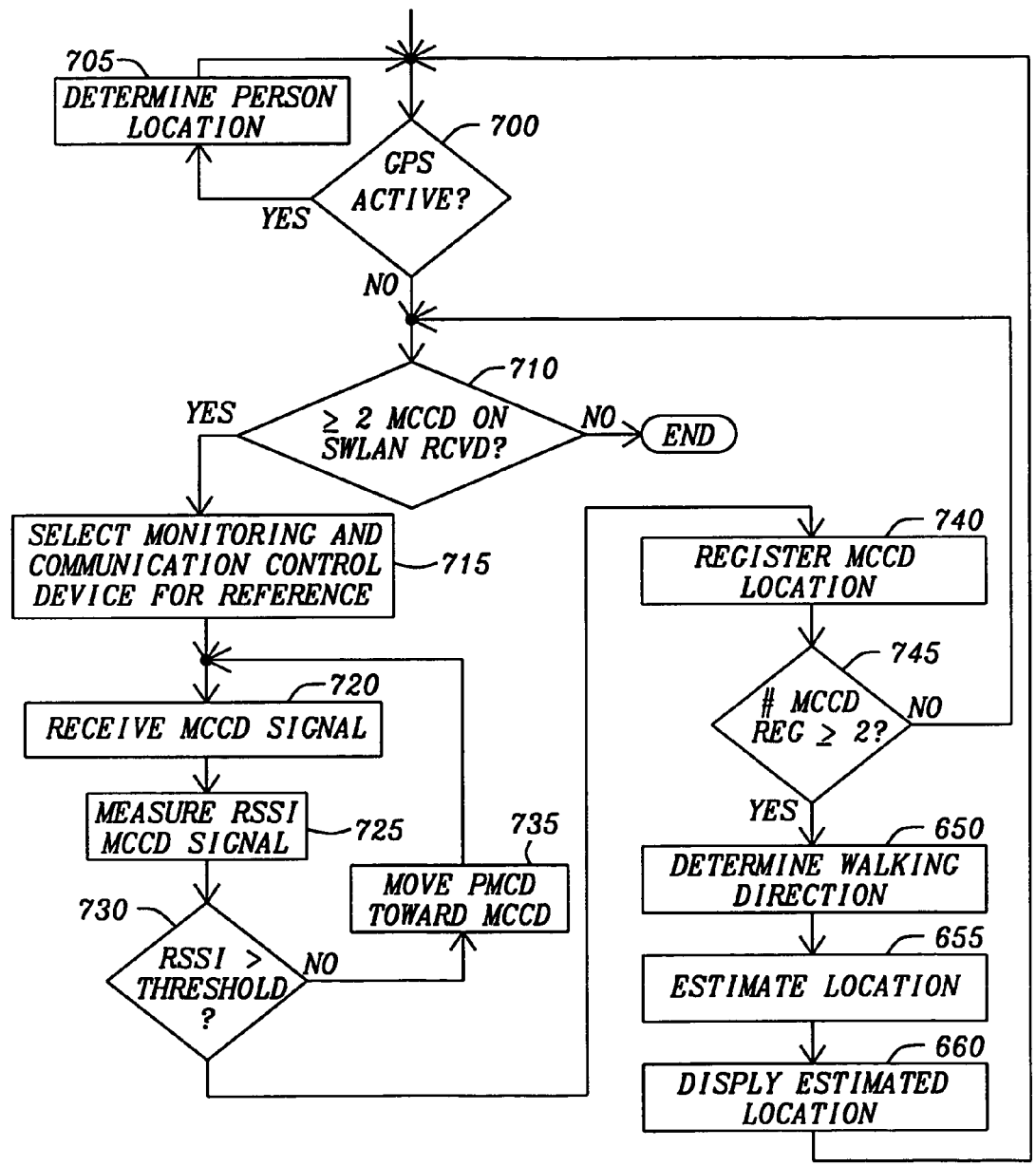
FIG. 10 is flowchart of an embodiment of a method for determining a location of a personal monitoring communication device of FIG. 2.
Figure 11:
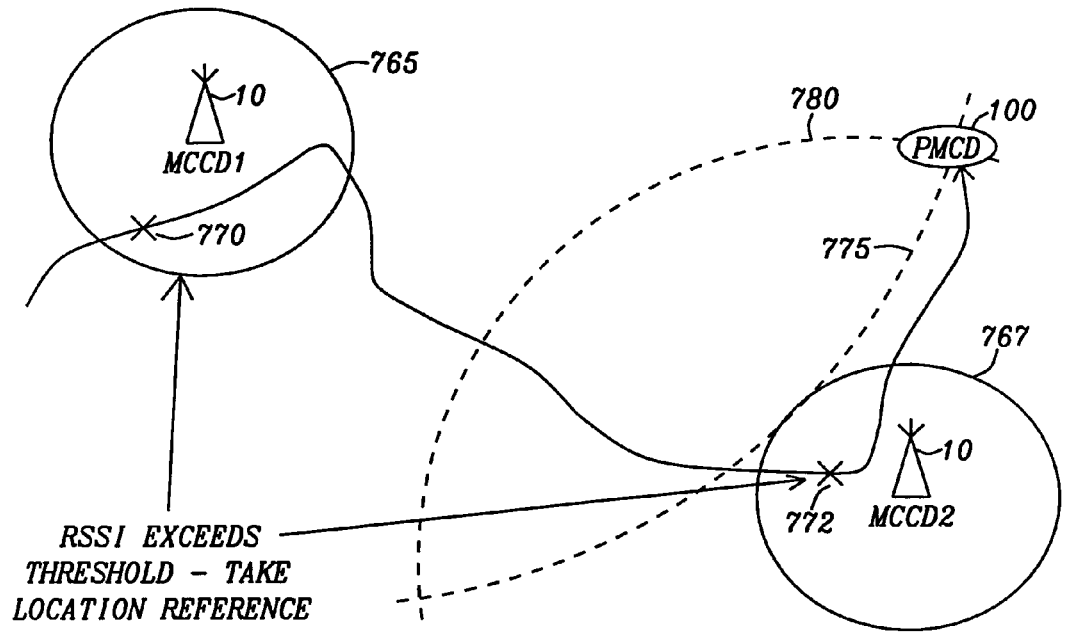
FIG. 11 is a diagram illustrating determining a reference location for the method of FIG. 10.

In some embodiments, the short range local area wireless network 114 is in communication with multiple monitoring and communication control devices 10 of FIG. 1. FIG. 10 is flowchart of a method for determining a location of a personal monitoring communication device 100 of FIG. 2 employing the receiver signal strength indicator (RSSI) of at least two monitoring and communication control devices 10. FIG. 11 is a diagram illustrating determining the reference location for the monitoring and communication control devices 10. As is known in the art, the RSSI is related to the power of the monitoring and communication control device 10, the receiver gain of the personal monitoring communication device 100, and the distance between the personal monitoring communication device 100 and the monitoring and communication control device 10.

Referring to FIGS. 2, 10, and 11, the method for relative location tracking begins with determining (Box 700) that the GPS unit 142 is active. If the GPS unit 142 is active, the person's location is determined (Box 705). If the GPS unit 142 is inactive, the personal monitoring communication device 100 determines (Box 710) if multiple monitoring and communication control devices 10 are in communication with the personal monitoring communication device 100 through the short range local area wireless network 114. If there are not two or more monitoring and communication control devices 10 in communication with the personal monitoring communication device 100, the process ends. If there are two or more monitoring and communication control devices 10 in communication with the personal monitoring communication device 100, one (MCCD1 or MCCD2 in FIG. 11) of the monitoring and communication control devices 10 is selected (Box 715) for registering as a reference location. The frequency hopping signal from the monitoring and communication control device 10 is received (Box 720) and the RSSI is measured (Box 725). The RSSI is compared (Box 730) to a threshold. If the RSSI is not greater than the threshold 765 or 767, the personal monitoring communication device 100 is not sufficiently close to the monitoring and communication control device 10 for registering as the reference location. The personal monitoring communication device 100 is moved (Box 735) toward the reference monitoring and communication control device 10. The frequency hopping signal from the monitoring and communication control device 10 is again received (Box 720) and the RSSI is measured (Box 725). The RSSI is compared (Box 730) to the threshold 765 or 767. If the RSSI is not greater than the threshold 765 or 767, the personal monitoring communication device 100 is moved (Box 735) closer to the reference monitoring and communication control device 10 until the RSSI is greater than the threshold 765 or 767. This indicates that the personal monitoring communication device 100 is within a relatively close distance 770 or 772 to the reference monitoring and communication control device 10 and the monitoring and communication control device 10 is registered (Box 740) as a reference location. The number of the monitoring and communication control device 10 is then determined (Box 745) if the greater than or equal to two. If the number is not greater than two, then the registering process is repeated for a second monitoring and communication control device 10 to be registered as a reference location. The number of monitoring and communication control device 10 registered as reference locations must be at least two and the number of the monitoring and communication control device 10 registered may be expanded as needed or available.

The person coupled to the personal monitoring communication device 100 may then move about. The RSSI of the registered monitoring and communication control devices 10 is measured (Box 750) and the distance of the personal monitoring communication device 100 to the registered monitoring and communication control devices 10 is calculated (Box 755). The distances define a contour for each of the distances 775 and 780 from the personal monitoring communication device 100 and the registered monitoring and communication control devices 10. The intersections of the contours of the distances 775 and 780 define the potential locations of the monitoring and communication control device 10. The potential locations are resolved by additional information provided by inertial navigation as described above. This results in the equivalence of triangulation with three reference points and therefore is uniquely defined.

In some embodiments, the personal monitoring communication device 100 reports the RSSI values of the received signals from the registered monitoring and communication control devices 10 to one of the monitoring and communication control devices 10. The monitoring and communication control device 10 then calculates the location of the personal monitoring communication device 100.

There are instances where the person being monitored by the personal monitoring communication device 100 may remove the device (e.g. Alzheimer patients or patients with other dementia disorders). The monitoring and communication control device 10 must be alerted that a person tampering with the personal monitoring communication device 100. A strap opening sensor is relatively simple to defeat by just closing the strap after removing it. To prevent the person simply removing the strap of the personal monitoring communication device 100, the personal monitoring communication device 100 must sense that the person is still coupled to the personal monitoring communication device 100. Referring to FIG. 2, the personal monitoring communication device 100 has a device-not-on-body detection circuit 144 that has a capacitive sensor 145. The capacitive sensor 145 determines if the personal monitoring communication device 100 remains coupled to the person due to the change in capacitance caused by water content in the human body.

Figure 12:
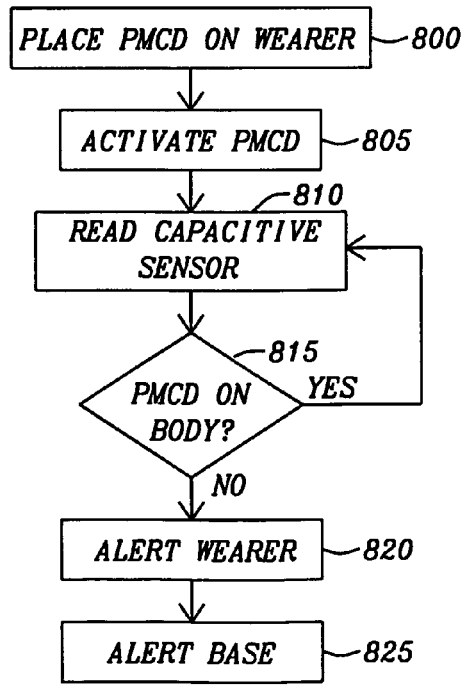
FIG. 12 is a flowchart of an embodiment of a method for determining that the personal monitoring communication device of FIG. 2 is coupled to a person being monitored.

FIG. 12 is a flowchart of a method for determining that the personal monitoring communication device 100 of FIG. 2 is coupled to a person being monitored. The personal monitoring communication device 100 is placed (Box 800) on the person to be monitored. The personal monitoring communication device 100 is activated (Box 805). At periodic intervals, the capacitive sensor 145 is read (Box 810) to determine (Box 815) if the person is coupled to the personal monitoring communication device 100. If the person is coupled to the personal monitoring communication device 100, at the next time interval, the capacitive sensor 145 is read (Box 810). If the person is no longer coupled to the personal monitoring communication device 100, the wearer is alerted (Box 820) to replace the personal monitoring communication device 100 and the monitoring and communication control device 10 is alerted (Box 825) that the person is no longer coupled to the associated personal monitoring communication device 100. The monitoring and communication control device 10 then alerts supervisory personnel to find the monitored person.

Figure 13:
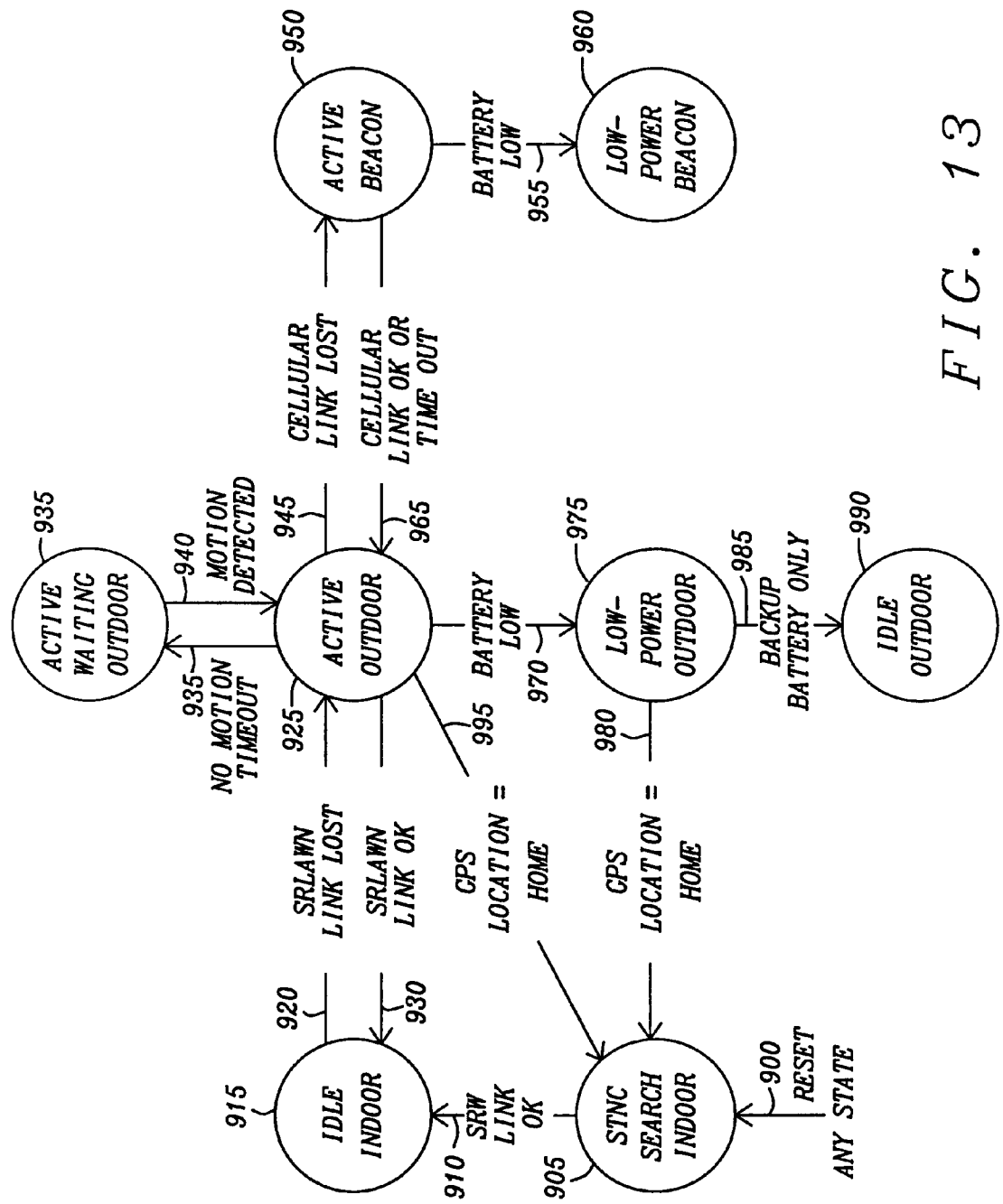
FIG. 13 is diagram of an embodiment of a finite state machine of a battery power management circuit of the personal monitoring communication device of FIG. 2.

As described above, the battery 148 of FIG. 2 is connected to a battery management and power distribution circuit 146 that monitors and controls the distribution of power to the circuits of the personal monitoring communication device 100 to appropriately activate and deactivate the circuits to extend the life of the battery 148. The FIG. 13 is a state diagram of a finite state machine of the battery power management circuit 146 of the personal monitoring communication device 100 of FIG. 2. FIG. 14 is a chart of the functions of the states of the finite state machine of FIG. 13. Refer now to FIGS. 2, 13, and 14. Any state of the finite state machine of the battery power management circuit 146 is transferred in the indoor synchronization search state 905 upon receiving a reset command 900. In the indoor synchronization search state 905, the personal monitoring communication device 100 is searching to receive a communication beacon from the short range local area wireless network 114 from the monitoring and communication control device 10. The cellular system 122 and the GPS unit 142 are active. The cellular modem 118 is establishing communications with the cellular system 122 and the GPS unit 142 is attempting to establish the location of the personal monitoring communication device 100. When the link to the short range local area wireless network 114 is established the battery power management circuit 146 is placed in the indoor idling state 915. In the indoor idling state 915, the personal monitoring communication device 100 is synchronized with the monitoring and communication control device 10 and the short range local area wireless network 114 is established. The cellular modem 118 and the GPS unit 142 are deactivated.

If the person moves the monitoring and communication control device 10 beyond the range of the short range local area wireless network 114 and the link is lost 920, the battery power management circuit 146 is placed in the active outdoor state 925. In active outdoor state 925, the short range local area wireless network modem 106 is deactivated to conserve power. The cellular modem 118 is activated to establish communications with the cellular system 122 and the GPS unit 142 is activated to establish the locations of the personal monitoring communication device 100. If the motion/fall detector 136 determines that the person is in not in motion for a predetermined period of time, the battery power management circuit 146 is place in the outdoor active waiting state 935. In the outdoor active waiting state 935 the short range local area wireless network modem 106 remains deactivated. The cellular modem 118 and the GPS unit 142 are placed in a standby state. The cellular modem maintains its link to the cellular system 122 and the GPS unit 142 assumes a state where the location signals from the GPS satellites are monitored, but the location is not determined. If the motion/fall detector 136 indicates that the person is in motion, the battery power management circuit 146 returns to the active outdoor state 925. The cellular modem 118 and the GPS unit 142 are placed in the active state.

If the cellular modem 118 loses 945 its link to the cellular system 122, the battery power management circuit 146 is placed in the activate beacon state 950. In the activate beacon state 950 the short range local area wireless network modem 106 activates the beacon such that the personal monitoring communication device finder 20 can locate the person coupled to the personal monitoring communication device 100. The cellular modem 118 is searching for the cellular signals to reestablish the link to the cellular system 122. The GPS unit 142 is deactivated. If the battery power management circuit 146 indicates that the energy level of the battery 148 is getting low 955, the battery power management circuit 146 enters the low power beacon state 960. In the low power beacon state 960, the short range local area wireless network modem 106, transmits the emergency beacon in a lower repetition rate to conserve energy. The cellular modem 118 and the GPS unit 142 are deactivated.

If during the transmission of the beacon in the active beacon state 950 the cellular modem 118 reestablishes 965 the link with the cellular system 122 or the active beacon state 950 times out, the battery power management circuit 146 reenters the active outdoor state 925. If the battery power management circuit 146 indicates that the battery 148 is becoming depleted 970 in energy, the battery power management circuit 146 enters the low power outdoor state 975. In the low power outdoor state 975, the short range local area wireless network modem 106 is deactivated and the cellular modem 118 and the GPS unit 142 are placed in the standby mode. If the battery power management circuit 146 indicates that the battery 148 is totally depleted of energy and is operating 985 on a backup battery, the battery power management circuit 146 enters the idle outdoor state 975. In the idle outdoor state 990, the short range local area wireless network modem 106 and the GPS unit 142 are deactivated and the cellular modem 118 is in the standby state. The battery power management circuit 146 is brought out of the idle outdoor state by replacement or charging of the battery 148 and resetting. The battery power management circuit 146 is reset by taking the personal monitoring communication device 100 out of range of the monitoring and communication control device 10 and returning the personal monitoring communication device 100 within range to initiate a synchronization search indoor when in range of the monitoring and communication control device 10.

If the battery power management circuit 146 is in the low power outdoor state 975 and the GPS unit 142 indicates that the person coupled with the personal monitoring communication device 100 is at the "home" location, the battery power management circuit 146 enters the indoor synchronization search state 905 where the personal monitoring communication device 100 is searching to receive a communication beacon from the short range local area wireless network 114 from the monitoring and communication control device 10. The cellular system 122 and the GPS unit 142 are active. The cellular modem 118 is establishing communications with the cellular system 122 and the GPS unit 142 is attempting to establish the location of the personal monitoring communication device 100. Upon establishing communications with the monitoring and communication control device 10, the personal monitoring is communication device 100 informs the personal monitoring communication device 100 that the battery 148 is nearly depleted of energy. The battery 148 is replaced or charged and the personal monitoring communication device 100 is reset.

If the battery power management circuit 146 is in the active outdoor state 925 and the GPS unit 142 indicates 995 that the personal monitoring communication device 100 is at the home location, the battery power management circuit 146 enters the indoor synchronization search state 905 to reestablish the link between the short range local area wireless network modem 106 and the short range local area wireless network 114.

The additional functions that provide the indoor dead reckoning, the emergency beacon to locate the personal monitoring communication device 100 when the GPS unit 142 and the link to the cellular system 122 is broken, the radio location, and the device-not-on body sensing are accomplished at very low costs. The same gyroscope and accelerometer hardware (combined cost ~$5 in the present technology) are used for motion detection for power control are used for the indoor location tracking using dead reckoning, and fall detection. Same short range local area wireless network modem 106 that is used for normal personal emergency response communication is also used for the emergency beacon for radiolocation and establishing location of the personal monitoring communication device 100.

While this invention has been particularly shown and described with reference to the preferred embodiments thereof, it will be understood by those skilled in the art that various changes in form and details may be made without departing from the spirit and scope of the invention.

The invention claimed is:

1. A personal monitoring and communication system comprises:
   at least one monitoring and communication control device;
   at least one personal monitoring communication device that is coupled with a person being monitored and is in communication with the at least on monitoring and communication control device, wherein the personal monitoring communication device comprises:
      a panic button which the person being monitored can activate in an emergency,
      a short range wireless radio transmitter/receiver in communication with the at least one monitoring and communication control device, and
      an emergency beacon generator that is connected to the panic button which when pressed by a person being monitored activates the emergency beacon generator that generates an emergency beacon frequency hopping signal at a slow frequency hopping rate and including an arbitrarily long pseudorandom bit sequence for transfer to the short range wireless radio transmitter/receiver for transmission; and
   a personal monitoring communication device finder comprising:
      a receiver for acquiring the emergency beacon frequency hopping signal,
      a slow frequency hopping sequence generator that provides a frequency sequence for the receiver that matches the slow frequency hopping rate to receive the emergency beacon frequency hopping signal,
      a frequency shift keying demodulator extracting the long pseudorandom bit sequence, and
      a correlator in communication with the frequency shift keying demodulator to receive the extracted long pseudorandom bit sequence and a local version of the long pseudorandom bit sequence for determining a sampling absolute correlation value for the extracted long pseudorandom bit sequence and the local long pseudorandom bit sequence to determine an estimate of the distance of the personal monitoring communication device finder to the personal monitoring communication device transmitting the emergency beacon.

2. The personal monitoring and communication system of claim 1 wherein the long pseudorandom bit sequence comprises:
 a bit repetition factor to maximize demodulation and detection by a receiver,
 a maximum length that is determined by a minimum signal bandwidth dictated by regulatory requirements wherein a product of a bit period multiplied by the repetition factor and the length of the long pseudorandom bit sequence determines a dwell time that complies with the regulatory requirements.

3. The personal monitoring and communication system of claim 2 wherein the dwell time is 0.4 seconds.

4. The personal monitoring and communication system of claim 1 wherein the distance is determined as a function of the personal monitoring communication device transmit power, a gain of the receiver of the personal monitoring communication device finder, and a propagation path loss model.

5. The personal monitoring and communication system of claim 1 wherein the personal monitoring communication device finder further comprises at least one directional antenna for determining a direction from the personal monitoring communication device finder to the personal monitoring communication device transmitting the emergency beacon.

6. The personal monitoring and communication system of claim 1 wherein the personal monitoring communication device finder further comprises a display for presenting the distance and direction from the personal monitoring communication device finder to the personal monitoring communication device transmitting the emergency beacon.

7. The personal monitoring and communication system of claim 1 wherein the personal monitoring communication device finder further comprises a sound producing device for presenting an audible indication of the distance and direction from the personal monitoring communication device finder to the personal monitoring communication device transmitting the emergency beacon.

8. The personal monitoring and communication system of claim 1 wherein the personal monitoring communication device finder is incorporated in the monitoring and communication control device for determining the location of a personal monitoring communication device transmitting an emergency beacon.

9. The personal monitoring and communication system of claim 1 wherein the personal monitoring communication device further comprises a dead reckoning circuit for determining the position of the person coupled to the personal monitoring communication device, the dead reckoning circuit comprises:
 a gyroscope for determining a direction that the person coupled to the personal monitoring communication device is moving;
 a three-axis accelerometer for determining an acceleration vector when the person moves;
 an integration unit in communication with the three axis accelerometer to receive the acceleration vector to double integrate the acceleration vector to determine a displacement from a reference location.

10. The personal monitoring and communication system of claim 9 wherein the short range wireless radio transmitter/receiver receives a signal from the monitoring and communication control device and from the signal, the dead reckoning device establishes a reference location from at least one monitoring and communication control device.

11. The personal monitoring and communication system of claim 10 wherein the dead reckoning circuit determines the reference location when a receiver signal strength indicator (RSSI) level for the signal received by the short range wireless radio transmitter/receiver from the monitoring and communication control device exceeds a threshold hold level.

12. The personal monitoring and communication system of claim 1 wherein the personal monitoring communication device further comprises a motion detection circuit for determining that the person to which the personal monitoring communication device is coupled is in motion, has not been in motion for an extended period of time, or has fallen.

13. The personal monitoring and communication system of claim 12 wherein the motion detection circuit comprises:
 a gyroscope for generating a direction signal indicating a direction that the person is moving;
 an three-axis accelerometer for generating signals indicating an acceleration vector indicating that the person is motion;
 a motion computation circuit coupled to the gyroscope and the three-axis accelerometer to receive the direction signal and the acceleration vector signals and determines if the person is in motion, or if the person has been inactive for an extended period of time, or if the person has fallen.

14. The personal monitoring and communication system of claim 13 wherein the gyroscope and the three-axis accelerometer measures motions to create displacement vectors that form a path that the personal monitoring and communication device has traveled.

15. The personal monitoring and communication system of claim 14 wherein averaging and low-pass filtering of the displacement data removes small scale changes and extracts large scale changes for location determination.

16. The personal monitoring and communication system of claim 1 wherein the personal monitoring communication device further comprising:
 a battery power management circuit connected to a battery for minimizing power consumption to increase battery life of the battery powering the personal monitoring communication devices, wherein the battery power management circuit comprises:
 a battery power sensing device for determining an amount of power remaining in the battery;
 a function status monitor connected to a plurality of personal monitoring communication device circuits; and
 a state machine in communication with the battery power sensing device and the function status monitor to determine which of the personal monitoring communication device circuits is deactivated or functionally degraded to conserve energy within the battery.

17. The personal monitoring and communication system of claim 16 wherein the personal monitoring communication device circuits comprise a global positioning system receiver, a cellular telephone radio transmitter/receiver, and the short range wireless radio transmitter/receiver and the motion detection circuit.

18. The personal monitoring and communication system of claim 17 wherein when the function status monitor determines that the short range wireless radio transmitter/receiver is in communication with a short range wireless radio transmitter/receiver of the monitoring and communication control device, the state machine instructs the global positioning system receiver and the cellular telephone radio transmitter/receiver to be deactivated.

19. The personal monitoring and communication system of claim 17 wherein when the function status monitor determines that the short range wireless radio transmitter/receiver is not in communication with a short range wireless radio transmitter/receiver of the monitoring and communication control device, the state machine instructs the global positioning system receiver and the cellular telephone radio transmitter/receiver to be activated.

20. The personal monitoring and communication system of claim 17 wherein when the function status monitor determines that the cellular telephone radio transmitter/receiver loses communication with the cellular telephone network, the state machine instructs the global positioning system receiver to be deactivated and the cellular telephone radio transmitter/receiver is placed into a network search mode or in a standby mode.

21. The personal monitoring and communication system of claim 17 wherein when the function status monitor determines that the cellular telephone radio transmitter/receiver has lost communication with the cellular telephone network, the state machine instructs that the emergency beacon be activated and transmitted on the short range wireless radio transmitter such that the personal monitoring communication device finder is able to locate the personal monitoring communication device.

22. The personal monitoring and communication system of claim 17 wherein when the function status monitor determines that the short range wireless radio transmitter/receiver is not in contact with the monitoring and communication control device, the state machine instructs the short range wireless radio transmitter/receiver to be deactivated.

23. The personal monitoring and communication system of claim 17 wherein when the function status monitor determines that the personal monitoring communication device is brought within a relatively close distance of the reference home location, the state machine instructs that the short range wireless radio transmitter/receiver be activated to establish contact with the monitoring and communication control device.

24. The personal monitoring and communication system of claim 17 wherein when the function status monitor determines that the motion detection circuit determines that the person coupled to the personal monitoring communication device is not in motion, the state machine instructs that the global positioning system receiver is deactivated.

25. The personal monitoring and communication system of claim 17 wherein when the function status monitor determines that the motion detection circuit determines that the person is in motion, state machine instructs that the global positioning system receiver is activated.

26. The personal monitoring and communication system of claim 17 wherein when the function status monitor determines that the battery sensing device indicates that the status of the battery has deteriorated to a first level, the state machine instructs that the personal monitoring communication device to reduce the location reporting frequency to the monitoring and communication control device and the cellular telephone radio transmitter/receiver and the global positioning system receiver be placed in a low-power standby mode for a longer period between the location reporting times.

27. The personal monitoring and communication system of claim 17 wherein when the function status monitor determines that the battery sensing device indicates that the status of the battery has deteriorated to a second level, the state machine instructs that the personal monitoring communication device place the cellular telephone radio transmitter/receiver in the low-power standby mode and the global positioning system receiver be disabled.

28. The personal monitoring and communication system of claim 27 wherein the cellular telephone radio transmitter/receiver is turned on when commanded through the cellular telephone network from the monitoring and communication control device.

29. The personal monitoring and communication system of claim 1 wherein the personal monitoring communication device has a tamper detection circuit to determine whether the personal monitoring communication device is coupled to the person being monitored.

30. The personal monitoring and communication system of claim 29 wherein the tamper detection circuit comprises:
a capacitive sensor that senses the presence of the person being monitored; and
a device-not-on-body reading circuit connected to the capacitive sensor to determine if the personal monitoring communication device is present such that when the personal monitoring communication device is not coupled to the person for a predetermined period of time an alert is triggered.

31. A personal monitoring communication device that is coupled with a person being monitored and is in communication with at least one monitoring and communication control device for monitoring and communicating with the person, wherein the personal monitoring communication device comprises:
a panic button which the person being monitored can activate in an emergency;
a short range wireless radio transmitter/receiver in communication with the at least one monitoring and communication control device; and
an emergency beacon generator that is connected to the panic button which when pressed by a person being monitored activates the emergency beacon generator that generates an emergency beacon frequency hopping signal at a slow frequency hopping rate and including an arbitrarily long pseudorandom bit sequence for transfer to the short range wireless radio transmitter/receiver for transmission;
wherein the long pseudorandom bit sequence comprises:
a bit repetition factor to maximize demodulation and detection by a receiver,
a maximum length that is determined by a minimum signal bandwidth dictated by regulatory requirements wherein a product of a bit period multiplied by the repetition factor and the length of the long pseudorandom bit sequence determines a dwell time that complies with the regulatory requirements.

32. The personal monitoring and communication device of claim 31 wherein the dwell time is 0.4 seconds.

33. The personal monitoring and communication device of claim 31 wherein the personal monitoring communication device is in communication with a personal monitoring communication device finder comprising:
a receiver for acquiring the emergency beacon frequency hopping signal;
a slow frequency hopping sequence generator that provides a frequency sequence for the receiver that matches the slow frequency hopping rate to receive the emergency beacon frequency hopping signal;
a frequency shift keying demodulator extracting the long pseudorandom bit sequence; and
a correlator in communication with the frequency shift keying demodulator to receive the extracted long pseudorandom bit sequence and a local version of the long pseudorandom bit sequence for determining a sampling absolute correlation value for the extracted long pseudorandom bit sequence and the local long pseudorandom bit sequence to determine an estimate of the distance of the personal monitoring communication device finder to the personal monitoring communication device transmitting the emergency beacon.

34. The personal monitoring and communication device of claim 33 wherein the distance is determined as a function of the personal monitoring communication device transmit power, a gain of the receiver of the personal monitoring communication device finder, and a propagation path loss model.

35. The personal monitoring and communication device of claim 33 wherein the personal monitoring communication device finder further comprises at least one directional antenna for determining a direction from the personal monitoring communication device finder to the personal monitoring communication device transmitting the emergency beacon.

36. The personal monitoring and communication device of claim 33 wherein the personal monitoring communication device finder further comprises a display for presenting the distance and direction from the personal monitoring communication device finder to the personal monitoring communication device transmitting the emergency beacon.

37. The personal monitoring and communication device of claim 33 wherein the personal monitoring communication device finder further comprises a sound producing device for presenting an audible indication of the distance and direction from the personal monitoring communication device finder to the personal monitoring communication device transmitting the emergency beacon.

38. The personal monitoring and communication device of claim 33 wherein the personal monitoring communication device finder is incorporated in the monitoring and communication control device for determining the location of a personal monitoring communication device transmitting an emergency beacon.

39. The personal monitoring and communication device of claim 31 further comprising a dead reckoning circuit for determining the position of the person coupled to the personal monitoring communication device, the dead reckoning circuit comprises:
a gyroscope for determining a direction that the person coupled to the personal monitoring communication device is moving;
a three-axis accelerometer for determining an acceleration vector when the person moves;
integration unit in communication with the three axis accelerometer to receive the acceleration vector to double integrate the acceleration vector to determine a displacement from a reference location.

40. The personal monitoring and communication device of claim 39 wherein the short range wireless radio transmitter/receiver receives a signal from the monitoring and communication control device and from the signal, the dead reckoning device establishes a reference location from at least one monitoring and communication control device.

41. The personal monitoring and communication device of claim 40 wherein the dead reckoning circuit determines the reference location when a receiver signal strength indicator (RSSI) level for the signal received by the short range wireless radio transmitter/receiver from the monitoring and communication control device exceeds a threshold hold level.

42. The personal monitoring and communication device of claim 31 further comprising a motion detection circuit for determining that the person to whom the personal monitoring communication device is coupled is in motion, has not been in motion for an extended period of time, or has fallen.

43. The personal monitoring and communication device of claim 42 wherein the motion detection circuit comprises:
a gyroscope for generating a direction signal indicating a direction that the person is moving;
an three-axis accelerometer for generating signals indicating an acceleration vector indicating that the person is motion;
a motion computation circuit coupled to the gyroscope and the three-axis accelerometer to receive the direction signal and the acceleration vector signals and determines if the person is in motion, or if the person has been inactive for an extended period of time, or if the person has fallen.

44. The personal monitoring and communication device of claim 43 wherein the gyroscope and the three-axis accelerometer measures motions to create displacement vectors that form a path that the personal monitoring and communication device has traveled.

45. The personal monitoring and communication device of claim 44 wherein averaging and low-pass filtering of the displacement data removes small scale changes and extracts large scale changes for location determination.

46. The personal monitoring and communication device of claim 31 further comprising:
a battery power management circuit connected to a battery for minimizing power consumption to increase battery life of the battery powering the personal monitoring communication devices, wherein the battery power management circuit comprises:
a battery power sensing device for determining an amount of power remaining in the battery;
a function status monitor connected to a plurality of personal monitoring communication device circuits; and
a state machine in communication with the battery power sensing device and the function status monitor to determine which of the personal monitoring communication device circuits is deactivated or functionally degraded to conserve energy within the battery.

47. The personal monitoring and communication device of claim 46 wherein the personal monitoring communication device circuits comprise a global positioning device receiver, a cellular telephone radio transmitter/receiver, and the short range wireless radio transmitter/receiver and the motion detection circuit.

48. The personal monitoring and communication device of claim 47 wherein when the function status monitor determines that the short range wireless radio transmitter/receiver is in communication with a short range wireless radio transmitter/receiver of the monitoring and communication control device, the state machine instructs the global positioning device receiver and the cellular telephone radio transmitter/receiver to be deactivated.

49. The personal monitoring and communication device of claim 47 wherein when the function status monitor determines that the short range wireless radio transmitter/receiver is not in communication with a short range wireless radio transmitter/receiver of the monitoring and communication control device the state machine instructs the global positioning device receiver and the cellular telephone radio transmitter/receiver to be activated.

50. The personal monitoring and communication device of claim 47 wherein when the function status monitor determines that the cellular telephone radio transmitter/receiver loses communication with the cellular telephone network, the state machine instructs the global positioning device receiver to be deactivated and the cellular telephone radio transmitter/receiver is placed into a network search mode or in a standby mode.

51. The personal monitoring and communication device of claim 47 wherein when the function status monitor determines that the cellular telephone radio transmitter/receiver has lost communication with the cellular telephone network, the state machine instructs that the emergency beacon be activated and transmitted on the short range wireless radio transmitter such that the personal monitoring communication device finder is able to locate the personal monitoring communication device.

52. The personal monitoring and communication device of claim 47 wherein when the function status monitor determines that the short range wireless radio transmitter/receiver is not in contact with the monitoring and communication control device, the state machine instructs the short range wireless radio transmitter/receiver to be deactivated.

53. The personal monitoring and communication device of claim 47 wherein when the function status monitor determines that the personal monitoring communication device is brought within a relatively close distance of the reference home location, the state machine instructs that the short range wireless radio transmitter/receiver be activated to establish contact with the monitoring and communication control device.

54. The personal monitoring and communication device of claim 47 wherein when the function status monitor determines that the motion detection circuit determines that the person coupled to the personal monitoring communication device is not in motion, the state machine instructs that the global positioning device receiver is deactivated.

55. The personal monitoring and communication device of claim 47 wherein when the function status monitor determines that the motion detection circuit determines that the person is in motion, state machine instructs that the global positioning device receiver is activated.

56. The personal monitoring and communication device of claim 47 wherein when the function status monitor determines that the battery sensing device indicates that the status of the battery has deteriorated to a first level, the state machine instructs the personal monitoring communication device to reduce the location reporting frequency to the monitoring and communication control device and the cellular telephone radio transmitter/receiver and the global positioning device receiver be placed in a low-power standby mode for a longer period between the location reporting times.

57. The personal monitoring and communication device of claim 47 wherein when the function status monitor determines that the battery sensing device indicates that the status of the battery has deteriorated to a second level, the battery state machine instructs that the personal monitoring communication device place the cellular telephone radio transmitter/receiver in the low-power standby mode and the global positioning device receiver be disabled.

58. The personal monitoring and communication device of claim 47 wherein the cellular telephone radio transmitter/receiver is turned on when commanded through the cellular telephone network from the monitoring and communication control device.

59. The personal monitoring and communication device of claim 31 further comprising a tamper detection circuit to determine whether the personal monitoring communication device is coupled to the person being monitored.

60. The personal monitoring and communication device of claim 59 wherein the tamper detection circuit comprises:

a capacitive sensor that senses the presence of the person being monitored; and
a device-not-on-body reading circuit connected to the capacitive sensor to determine if the personal monitoring communication device is present such that when the personal monitoring communication device is not coupled to the person for a predetermined period of time an alert is triggered.

61. A personal monitoring communication device finder in communication with a personal monitoring communication device comprising:
a receiver for acquiring the emergency beacon frequency hopping signal transmitted by the personal monitoring communication device;
a slow frequency hopping sequence generator that provides a frequency sequence for the receiver that matches the slow frequency hopping rate to receive the emergency beacon frequency hopping signal;
a frequency shift keying demodulator extracting a long pseudorandom bit sequence from the acquired emergency beacon frequency hopping signal; and
a correlator in communication with the frequency shift keying demodulator to receive the extracted long pseudorandom bit sequence and a local version of the long pseudorandom bit sequence for determining a sampling absolute correlation value for the extracted long pseudorandom bit sequence and the local long pseudorandom bit sequence to determine an estimate of the distance of the personal monitoring communication device finder to the personal monitoring communication device transmitting the emergency beacon.

62. The personal monitoring communication device finder of claim 61 wherein the personal monitoring communication device is coupled with a person being monitored wherein the personal monitoring communication device comprises:
a panic button which the person being monitored can activate in an emergency;
a short range wireless radio transmitter/receiver in communication with the at least one monitoring and communication control device; and
an emergency beacon generator that is connected to the panic button which when pressed by a person being monitored activates the emergency beacon generator that generates the emergency beacon frequency hopping signal at a slow frequency hopping rate and including an arbitrarily long pseudorandom bit sequence to the short range wireless radio transmitter/receiver for transmission.

63. The personal monitoring communication device finder of claim 62 wherein the long pseudorandom bit sequence comprises:
a bit repetition factor to maximize demodulation and detection by a receiver,
a maximum length that is determined by a minimum signal bandwidth dictated by regulatory requirements wherein a product of a bit period multiplied by the repetition factor and the length of the long pseudorandom bit sequence determines a dwell time that complies with the regulatory requirements.

64. The personal monitoring and communication device finder of claim 63 wherein the dwell time is 0.4 seconds.

65. The personal monitoring and communication device finder of claim 61 a wherein the distance is determined as a function of the personal monitoring communication device transmit power, a gain of the receiver of the personal monitoring communication device finder, and a propagation path loss model.

66. The personal monitoring and communication device finder of claim 65 further comprising at least one directional antenna for determining a direction from the personal monitoring communication device finder to the personal monitoring communication device transmitting the emergency beacon.

67. The personal monitoring and communication device finder of claim 66 wherein the personal monitoring communication device finder further comprises a display for presenting the distance and direction from the personal monitoring communication device finder to the personal monitoring communication device transmitting the emergency beacon.

68. The personal monitoring and communication device finder of claim 66 wherein the personal monitoring communication device finder further comprises a sound producing device for presenting an audible indication of the distance and direction from the personal monitoring communication device finder to the personal monitoring communication device transmitting the emergency beacon.

69. The personal monitoring and communication device finder of claim 66 wherein the personal monitoring communication device finder is incorporated in the monitoring and communication control device for determining the location of a personal monitoring communication device transmitting an emergency beacon.

70. A dead reckoning circuit incorporated within a personal monitoring and communication device for determining the position of the person coupled to the personal monitoring communication device, the dead reckoning circuit comprising:
- a gyroscope configured for determining a direction that the person coupled to the personal monitoring communication device is moving;
- a three-axis accelerometer configured for determining an acceleration vector when the person moves; and
- an integration unit in communication with the three axis accelerometer configured for receiving the acceleration vector and configured for double integrating the acceleration vector to determine displacement data indicative of displacement from a reference location to determine a path that the personal monitoring and communication system has traveled;
- wherein the integration unit is configured for averaging and low-pass filtering of the displacement data for removing small scale changes and extracting large scale changes for noise of random movements of the personal monitoring and communication device.

71. The dead reckoning circuit of claim 70 wherein the dead reckoning circuit is in communication with a short range wireless radio transmitter/receiver and configured for receiving a signal from at least one monitoring and communication control device and from the signal the dead reckoning device establishes a reference location from at least one monitoring and communication control device.

72. The dead reckoning circuit of claim 71 wherein the dead reckoning circuit determines the reference location when a receiver signal strength indicator (RSSI) level for the signal received by the short range wireless radio transmitter/receiver from the monitoring and communication control device exceeds a threshold hold level.

73. A motion detection circuit within a personal monitoring communication device for determining that the person to which the personal monitoring communication device is coupled is in motion has no been in motion for an extended period of time, or has fallen, comprising:
- a gyroscope configured for generating a direction signal indicating a direction that the person is moving;
- an three-axis accelerometer configured for generating signals indicating an acceleration vector indicating that the person is motion;
- a motion computation circuit coupled to the gyroscope and the three-axis accelerometer configured for receiving the direction signal and the acceleration vector signals, configured for measuring motions to create displacement vectors that form a path that the personal monitoring and communication system has traveled, and configured for determining, if the person is in motion, or if the person has been inactive for an extended period of time, or if the person has fallen;
- wherein the motion computation circuit is configured for averaging and low-pass filtering of the displacement data removes small scale changes and extracts large scale changes for location determination.

74. A battery power management circuit incorporated in on a personal monitoring and communication device connected to a battery for minimizing power consumption to increase battery life of the battery powering the personal monitoring communication device, wherein the battery power management circuit comprises:
- a battery power sensing device for determining an amount of power remaining in the battery;
- a function status monitor connected to a plurality of personal monitoring communication device circuits, wherein the plurality of personal monitoring communication device circuits comprises a global positioning device receiver, a cellular telephone radio transmitter/receiver, a short range wireless radio transmitter/receiver and a motion detection circuit; and
- a state machine in communication with the battery power sensing device and the function status monitor to determine which of the personal monitoring communication device circuits is deactivated or functionally degraded to conserve energy within the battery;
- wherein when the function status monitor determines that the short range wireless radio transmitter/receiver is in communication with a short range wireless radio transmitter/receiver of the monitoring and communication control device, the state machine instructs the global positioning device receiver and the cellular telephone radio transmitter/receiver to be deactivated.

75. The battery power management circuit of claim 74 wherein when the function status monitor determines that the short range wireless radio transmitter/receiver is not in communication with a short range wireless radio transmitter/receiver of the monitoring and communication control device the state machine instructs the global positioning device receiver and the cellular telephone radio transmitter/receiver to be activated.

76. The battery power management circuit of claim 74 wherein when the function status monitor determines the cellular telephone radio transmitter/receiver loses communication with the cellular telephone network, the state machine instructs the global positioning device receiver to be deactivated and the cellular telephone radio transmitter/receiver is placed into a network search mode or in a standby mode.

77. The battery power management circuit of claim 74 wherein when the function status monitor determines that the cellular telephone radio transmitter/receiver has lost communication with the cellular telephone network, the state machine instructs that the emergency beacon be activated and transmitted on the short range wireless radio transmitter such that the personal monitoring communication device finder is able to locate the personal monitoring communication device.

78. The battery power management circuit of claim 74 wherein when the function status monitor determines that the short range wireless radio transmitter/receiver is not in contact with the monitoring and communication control device, the state machine instructs the short range wireless radio transmitter/receiver to be deactivated.

79. The battery power management circuit of claim 74 wherein when the function status monitor determines that the personal monitoring communication device is brought within a relatively close distance of the reference home location, the state machine instructs that the short range wireless radio transmitter/receiver be activated to establish contact with the monitoring and communication control device.

80. The battery power management circuit of claim 74 wherein when the function status monitor determines that the motion detection circuit determines that the person coupled to the personal monitoring communication device is not in motion, the state machine instructs that the global positioning device receiver is deactivated.

81. The battery power management circuit of claim 74 wherein when the function status monitor determines that the motion detection circuit determines that the person is in motion, state machine instructs that the global positioning device receiver is activated.

82. The battery power management circuit of claim 74 wherein when the function status monitor determines that the battery sensing device indicates that the status of the battery has deteriorated to a first level, the state machine instruct the personal monitoring communication device to reduce the location reporting frequency to the monitoring and communication control device and the cellular telephone radio transmitter/receiver and the global positioning device receiver be placed in a low-power standby mode for a longer period between the location reporting times.

83. The battery power management circuit of claim 74 wherein when the function status monitor determines that the battery sensing device indicates that the status of the battery has deteriorated to a second level, the battery state machine instructs that the personal monitoring communication device place the cellular telephone radio transmitter/receiver in the low-power standby mode and the global positioning device receiver be disabled.

84. The battery power management circuit of claim 74 wherein the cellular telephone radio transmitter/receiver is turned on when commanded through the cellular telephone network from the monitoring and communication control device.

85. The battery power management circuit of claim 74 further comprising a tamper detection circuit to determine whether the personal monitoring communication device is coupled to the person being monitored.

\* \* \* \* \*